United States Patent
Wu

(10) Patent No.: US 10,739,350 B2
(45) Date of Patent: *Aug. 11, 2020

(54) METHOD FOR DETERMINING ANALYTE CONCENTRATION BASED ON SLOPE-BASED COMPENSATION

(75) Inventor: Huan-Ping Wu, Granger, IN (US)

(73) Assignee: Ascensia Diabetes Care Holdings AG, Basel (CH)

(*) Notice: Subject to any disclaimer, the term of this patent is extended or adjusted under 35 U.S.C. 154(b) by 2035 days.

This patent is subject to a terminal disclaimer.

(21) Appl. No.: 12/329,698

(22) Filed: Dec. 8, 2008

(65) Prior Publication Data
US 2009/0177406 A1 Jul. 9, 2009

Related U.S. Application Data

(60) Provisional application No. 61/012,716, filed on Dec. 10, 2007.

(51) Int. Cl.
G01N 33/66 (2006.01)
G01N 27/327 (2006.01)

(52) U.S. Cl.
CPC ......... G01N 33/66 (2013.01); G01N 27/3273 (2013.01)

(58) Field of Classification Search
None
See application file for complete search history.

(56) References Cited

U.S. PATENT DOCUMENTS

| | | | |
|---|---|---|---|
| 4,431,004 A | 2/1984 | Bessman et al. | |
| 4,750,496 A | 6/1988 | Reinhart et al. | |
| 5,243,516 A | 9/1993 | White | |
| 5,366,609 A | 11/1994 | White et al. | |
| 5,395,504 A | 3/1995 | Saurer et al. | |
| 5,508,171 A | 4/1996 | Walling et al. | |
| 5,620,579 A | 4/1997 | Genshaw et al. | |
| 5,653,863 A | 8/1997 | Genshaw et al. | |
| 5,723,284 A | 3/1998 | Ye | |
| 5,798,031 A | 8/1998 | Charlton et al. | |
| 6,120,676 A | 9/2000 | Heller et al. | |
| 6,153,069 A | 11/2000 | Pottgen et al. | |
| 6,233,471 B1 | 5/2001 | Berner et al. | |
| 6,275,717 B1 | 8/2001 | Gross et al. | |
| 6,391,645 B1 | 5/2002 | Huang et al. | |
| 6,413,411 B1 | 7/2002 | Pottgen et al. | |
| 6,576,117 B1 | 6/2003 | Iketaki | |
| 6,645,368 B1 | 11/2003 | Beaty et al. | |
| 6,824,670 B2 | 11/2004 | Tokunaga et al. | |
| 7,122,111 B2 | 10/2006 | Tokunaga et al. | |
| 7,132,041 B2 | 11/2006 | Deng | |
| 7,338,639 B2* | 3/2008 | Burke et al. | 422/82.01 |
| 7,351,323 B2 | 4/2008 | Iketaki et al. | |
| 7,501,052 B2 | 3/2009 | Iyenga et al. | |
| 7,517,439 B2 | 4/2009 | Harding et al. | |
| 7,781,222 B2* | 8/2010 | Wu et al. | 436/147 |
| 2004/0072158 A1 | 4/2004 | Henkens et al. | |
| 2004/0079652 A1 | 4/2004 | Vreke et al. | |
| 2004/0256248 A1 | 12/2004 | Burke et al. | |
| 2004/0260511 A1 | 12/2004 | Burke et al. | |
| 2005/0176153 A1 | 8/2005 | O'hara et al. | |
| 2007/0231914 A1 | 10/2007 | Deng et al. | |
| 2008/0248581 A1 | 10/2008 | Chu et al. | |

FOREIGN PATENT DOCUMENTS

| | | |
|---|---|---|
| CN | 1558224 A | 12/2004 |
| EP | 1742045 | 1/2007 |
| JP | 2005147990 | 6/2005 |
| JP | 2006-239062 A | 9/2006 |
| JP | 2009-528540 A | 8/2009 |
| WO | 1996014026 | 10/1995 |
| WO | 1998058250 | 12/1998 |
| WO | WO 1999/60391 | 11/1999 |
| WO | 2001021827 | 3/2001 |
| WO | 2006042304 | 4/2005 |
| WO | 2006079797 | 8/2006 |
| WO | 2007013915 | 2/2007 |
| WO | 2007014231 | 2/2007 |
| WO | 2007040913 | 4/2007 |
| WO | WO 2007/100651 | 9/2007 |
| WO | WO 2007/133985 | 11/2007 |

OTHER PUBLICATIONS

Lee et al. (Proceedings of IGARSS '89; Jul. 10-14, 1989. pp. 1005-1008).*
Panteleon et al. (Diabetes Technology & Therapeutics, May 2003, 5(3): 401-41).*
International Searching Authority, "International Search Report and Written Opinion for PCT/US2006/028013", dated Dec. 6, 2006, Publisher: European Patent Office, Published in: EP.
International Searching Authority, "International Search Report and Written Opinion for PCT/US2007/068320", dated Oct. 19, 2007, Publisher: European Patent Office, Published in: EP.
International Searching Authority, "International Search Report and Written Opinion for PCT/US2008/085768", dated Sep. 28, 2009, Publisher: European Patent Office, Published in: EP.
Gunasingham, et al., "Pulsed amperometric detection of glucose using a mediated enzyme electrode", "Journal of Electroanalytical Chemistry", 1990, pp. 349-362, vol. 287, No. 2.

(Continued)

Primary Examiner — Pablo S Whaley
(74) Attorney, Agent, or Firm — Nixon Peabody LLP

(57) ABSTRACT

A biosensor system determines analyte concentration from an output signal generated from a light-identifiable species or a redox reaction of the analyte. The biosensor system adjusts a correlation for determining analyte concentrations from output signals with one or more index functions extracted from the output signals. The index functions determine at least one slope deviation value, $\Delta S$, or normalized slope deviation from one or more error parameters. The slope-adjusted correlation between analyte concentrations and output signals may be used to determine analyte concentrations having improved accuracy and/or precision from output signals including components attributable to bias.

27 Claims, 18 Drawing Sheets

(56) References Cited

OTHER PUBLICATIONS

Lin, et al., "Reduction of the Interferences of Biochemicals and Hematrocrit Ratio on the Determination of Whole Blood Glucose Using", "Anal. Bioanal. Chem.", 2007, pp. 1623-1631, vol. 289.

* cited by examiner

METHOD FOR DETERMINING ANALYTE CONCENTRATION BASED ON SLOPE-BASED COMPENSATION

REFERENCE TO RELATED APPLICATIONS

This application claims the benefit of U.S. Provisional Application No. 61/012,716 entitled "Slope-Based Compensation" filed Dec. 10, 2007, which is incorporated by reference in its entirety.

BACKGROUND

Biosensor systems provide an analysis of a biological fluid, such as whole blood, serum, plasma, urine, saliva, interstitial, or intracellular fluid. Typically, the systems include a measurement device that analyzes a sample residing in a sensor strip. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor system to determine the glucose level in whole blood for adjustments to diet and/or medication.

Biosensor systems may be designed to analyze one or more analytes and may use different volumes of biological fluids. Some systems may analyze a single drop of whole blood, such as from 0.25-15 microliters (μL) in volume. Biosensor systems may be implemented using bench-top, portable, and like measurement devices. Portable measurement devices may be hand-held and allow for the identification and/or quantification of one or more analytes in a sample. Examples of portable measurement systems include the Ascensia® Breeze® and Elite® meters of Bayer Health-Care in Tarrytown, N.Y., while examples of bench-top measurement systems include the Electrochemical Workstation available from CH Instruments in Austin, Tex.

Biosensor systems may use optical and/or electrochemical methods to analyze the biological fluid. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical method. In either optical system, the system measures and correlates the light with the analyte concentration of the sample.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical detector fluoresces or emits light in response to the analyte redox reaction. A detector collects and measures the generated light (output signal). The amount of light produced by the chemical indicator is an indication of the analyte concentration in the sample.

In electrochemical biosensor systems, the analyte concentration is determined from an electrical signal generated by an oxidation/reduction or redox reaction of the analyte or a species responsive to the analyte when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from a first species to a second species during the redox reaction. The enzyme or similar species may react with a single analyte, thus providing specificity to a portion of the generated output signal. A mediator may be used to maintain the oxidation state of the enzyme.

Electrochemical biosensor systems usually include a measurement device having electrical contacts that connect with electrical conductors in the sensor strip. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The measurement device applies an input signal through the electrical contacts to the electrical conductors of the sensor strip. The electrical conductors convey the input signal through the electrodes into the sample present in the sample reservoir. The redox reaction of the analyte generates an electrical output signal in response to the input signal. The electrical output signal from the strip may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the biological fluid.

In coulometry, a potential is applied to the sample to exhaustively oxidize or reduce the analyte. A biosensor system using coulometry is described in U.S. Pat. No. 6,120,676. In amperometry, an electrical signal of constant potential (voltage) is applied to the electrical conductors of the sensor strip while the measured output signal is a current. Biosensor systems using amperometry are described in U.S. Pat. Nos. 5,620,579; 5,653,863; 6,153,069; and 6,413,411. In voltammetry, a varying potential is applied to a sample of biological fluid. In gated amperometry and gated voltammetry, pulsed inputs are used as described in WO 2007/013915 and WO 2007/040913, respectively.

In many biosensor systems, the sensor strip may be adapted for use outside, inside, or partially inside a living organism. When used outside a living organism, a sample of the biological fluid may be introduced into a sample reservoir in the sensor strip. The sensor strip may be placed in the measurement device before, after, or during the introduction of the sample for analysis. When inside or partially inside a living organism, the sensor strip may be continually immersed in the sample or the sample may be intermittently introduced to the strip. The sensor strip may include a reservoir that partially isolates a volume of the sample or be open to the sample. When open, the strip may take the form of a fiber or other structure placed in contact with the biological fluid. Similarly, the sample may continuously flow through the strip, such as for continuous monitoring, or be interrupted, such as for intermittent monitoring, for analysis.

The measurement performance of a biosensor system is defined in terms of accuracy and/or precision. Increases in accuracy and/or precision provide for an improvement in measurement performance, a reduction in the bias, of the system. Accuracy may be expressed in terms of bias of the sensor system's analyte reading in comparison to a reference analyte reading, with larger bias values representing less accuracy. Precision may be expressed in terms of the spread or variance of the bias among multiple analyte readings in relation to a mean. Bias is the difference between one or more values determined from the biosensor system and one or more accepted reference values for the analyte concentration in the biological fluid. Thus, one or more errors in the measured analysis results in the bias of the determined analyte concentration of a biosensor system. Bias may be expressed in terms of "absolute bias" or "percent bias". Absolute bias may be expressed in the units of the measurement, such as mg/dL, while percent bias may be expressed as a percentage of the absolute bias value over the reference value. Accepted reference values may be obtained with a reference instrument, such as the YSI 2300 STAT PLUS™ available from YSI Inc., Yellow Springs, Ohio.

Biosensor systems may provide an output signal during the analysis of the biological fluid that includes one or multiple errors. These errors may be reflected in an abnormal output signal, such as when one or more portions or the entire output signal is non-responsive or improperly responsive to the analyte concentration of the sample. These errors may be from one or more contributors, such as the physical characteristics of the sample, the environmental aspects of the sample, the operating conditions of the system, interfering substances, and the like. Physical characteristics of the sample include hematocrit (red blood cell) concentration and the like. Environmental aspects of the sample include temperature and the like. Operating conditions of the system include underfill conditions when the sample size is not large enough, slow-filling of the sample, intermittent electrical contact between the sample and one or more electrodes in the sensor strip, degradation of the reagents that interact with the analyte, and the like. Interfering substances include ascorbic acid, uric acid, acetaminophen, and the like. There may be other contributors or a combination of contributors that cause errors.

Many biosensor systems include one or more methods to correct errors associated with an analysis. The concentration values obtained from an analysis with an error may be inaccurate. Thus, the ability to correct these inaccurate analyses may increase the accuracy of the concentration values obtained. An error correction system may compensate for one or more errors, such as a sample temperature or sample hematocrit content, which is different from a reference temperature or reference hematocrit value. For example, conventional biosensor systems may be configured to report glucose concentrations presuming a 40% (v/v) hematocrit content for a whole blood sample, regardless of the actual hematocrit content of the sample. In these systems, any glucose measurement performed on a blood sample containing less or more than 40% hematocrit will include error and thus have bias attributable to the hematocrit effect.

Some biosensor systems have an error correction system that compensates for different hematocrit concentrations in the sample. Various methods and techniques have been proposed to reduce the bias of the hematocrit effect on glucose measurements. Some methods use the ratio of currents from a forward and a reverse potential pulse to compensate for the hematocrit effect. Other methods have been proposed to reduce the bias of the hematocrit effect, including using silica particles to filter red blood cells from the electrode surface or using wide electrode spacing in combination with mesh layers to distribute blood throughout the sensor strip.

Some biosensor systems have an error correction system that compensates for temperature. Such error compensation systems typically alter a determined analyte concentration for a particular reference temperature in response to an instrument or sample temperature. A number of biosensor systems compensate for temperature by correcting the output signal prior to calculating the analyte concentration from a correlation equation. Other biosensor systems compensate for temperature by correcting the analyte concentration calculated by the correlation equation. Generally, conventional methods of temperature compensation look at the effect of temperature on a specific parameter, not the overall effect the error has on the bias of the analysis. Biosensor systems having error detection and/or compensation systems for the sample temperature are described in U.S. Pat. Nos. 4,431,004; 4,750,496; 5,366,609; 5,395,504; 5,508,171; 6,391,645; and 6,576,117.

Some biosensor systems have an error correction system that compensates for interferents and other contributors. Such error correction systems typically use an electrode lacking one or more of the working electrode reagents to allow for the subtraction of a background interferent signal from the working electrode signal.

While conventional error compensation systems balance various advantages and disadvantages, none are ideal. Conventional systems usually are directed to detect and respond to a particular type of error, either temperature or hematocrit, for example. Such systems typically do not have the ability to compensate for multiple error sources. These systems generally also lack the ability to alter the compensation for the error based on the output signal from a specific sample. Consequently, conventional biosensor systems may provide analysis results having determined analyte concentration values outside a desired performance limit. Accordingly, there is an ongoing need for improved biosensor systems, especially those that may provide increasingly accurate and/or precise determination of the concentration of the analyte in the sample. The systems, devices, and methods of the present invention overcome at least one of the disadvantages associated with conventional biosensor systems.

SUMMARY

The present invention provides a biosensor system that adjusts a relation for determining analyte concentrations in a biological sample from output signals with one or more index functions responsive to one or more errors that could bias the determined analyte concentrations. The bias may be represented by slope deviations, ΔS values, and normalized slope deviations obtained from one or more error parameters. The ΔS values represent slope deviations determined with one or more index functions from the error parameters. The index functions are extracted from the output signals.

In a method for determining an analyte concentration in a sample, an output signal value responsive to the concentration of the analyte in the sample is generated. At least one ΔS value from at least one error parameter is determined, and the at least one output signal value is compensated with at least one reference correlation and at least one ΔS value to determine the analyte concentration in the sample. The at least one ΔS value may be determined from an index function f(Index). The f(Index) relates at least one error parameter to ΔS. The reaction may be an electrochemical redox reaction.

In a method for determining index functions from error parameters, at least one error parameter responsive to the percent bias in a determined analyte concentration in a sample is determined. The at least one error parameter is related to at least one ΔS value with at least one index function, the at least one ΔS value representing the difference in slope between the slope from a reference correlation and a hypothetical slope of a line for the output signal value that would provide an analyte concentration in the sample without bias.

A biosensor system for determining an analyte concentration in a sample includes a measurement device and sensor strip. The measurement device has a processor connected to a sensor interface and to a storage medium. The sensor strip has a sample interface adjacent to a reservoir formed by the strip. The processor determines an output signal value responsive to the concentration of the analyte in the sample from the sensor interface. The processor determines at least one ΔS value from an error parameter and compensates the output signal value with the at least one ΔS value and at least one reference correlation present in the storage medium.

A biosensor system adjusts a correlation between analyte concentrations and output signals with at least one ΔS value in response to error parameters. The processor determines an analyte concentration from the slope-adjusted correlation in response to an output signal from the sample interface.

In another method for determining an analyte concentration in a sample, one or more output signals are generated from a sample. One or more index functions are determined. Where the index functions are responsive to at least one error parameter. The analyte concentration in the sample is determined from the output signals in response to the index functions.

A further method for determining an analyte concentration in a sample, one or more potential sequences are applied to the sample. One or more output signals are recorded from the sample. One or more index functions are determined. The analyte concentration in the sample is determined from the output signals in response to the one index functions.

Other systems, methods, features, and advantages of the invention will be, or will become, apparent to one with skill in the art upon examination of the following figures and detailed description. It is intended that all such additional systems, methods, features and advantages be included within this description, be within the scope of the invention, and be protected by the claims that follow

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION

A biosensor system adjusts a correlation for determining analyte concentrations in a biological sample from output signals with index functions extracted from intermediate signals of the output signals. The analyte may generate the output signals in response to a light-identifiable species or a redox reaction. The intermediate signals may be one or more portions of the output signals or the like. Index functions compensate the correlation for determining analyte concentrations from the output signals for one or more errors in the analyses that could result in bias of the determined analyte concentrations.

Index functions correspond to the %-bias in the correlation between the analyte concentrations and the output signals due to one or more errors in the analysis. The %-bias in the correlation may be represented by one or more $\Delta S$ values obtained from one or more error parameters. The $\Delta S$ values represent slope deviations of the correlation between analyte concentrations and output signals determined from one or more error parameters. Index functions corresponding to the slope or change in slope may be normalized to reduce the statistical effect of changes in the output signals, improve the differentiation in variations of the output signals, standardize the measurements of the output signals, a combination thereof, or the like. Other index functions may be used. The adjusted correlation may be used to determine analyte concentrations in biological samples from the output signals and may have improved accuracy and/or precision in comparison to conventional biosensors. While the compensation system provides substantial benefits when analyzing complex biological samples, the compensation system may be used to improve the accuracy and/or precision of other types of analysis.

Figure 1:
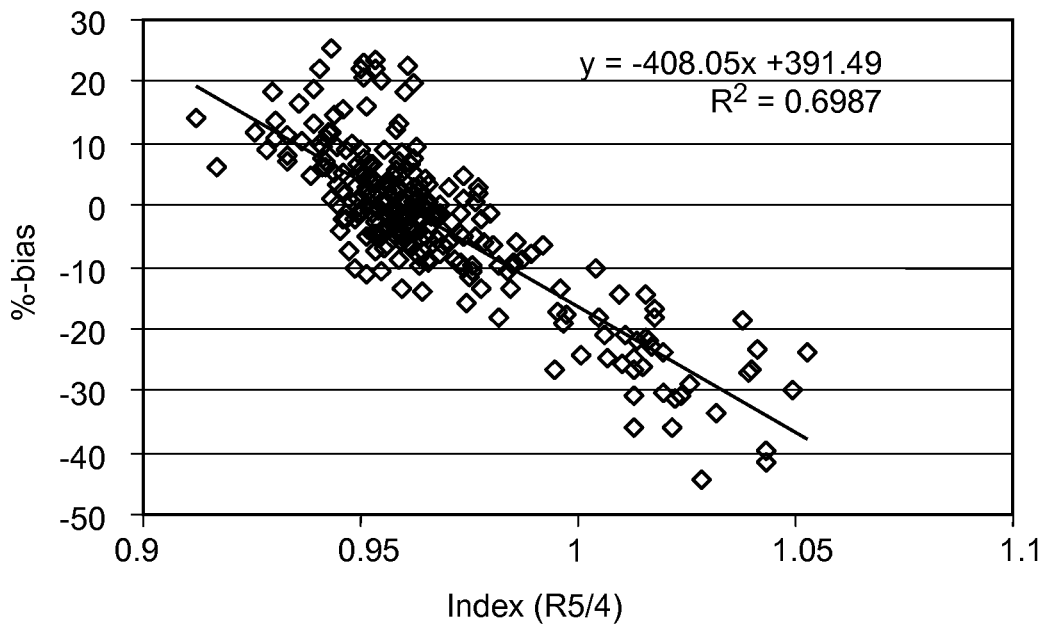
FIG. 1 depicts the correlation between %-bias and an index function based on a ratio parameter.
Figure 2:
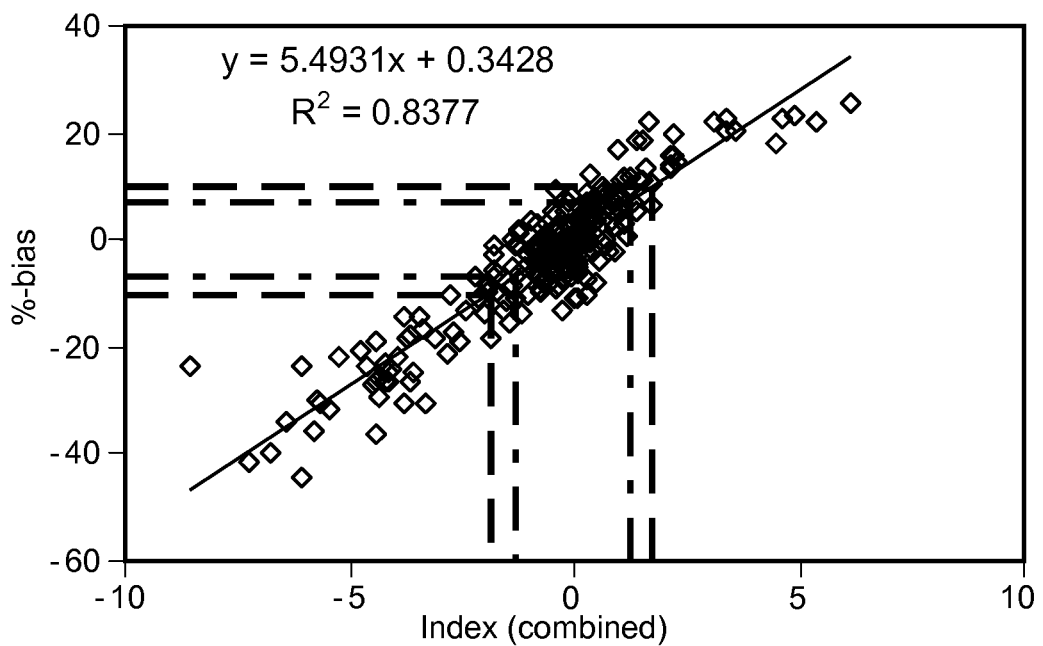
FIG. 2 depicts the correlation between %-bias and a combination of index functions.

FIGS. 1 and 2 depict correlations between the %-bias and indices or index functions extracted from output signals of an analyte concentration analysis. In this example, the analyte generates output signals in response to the pulse sequence of a gated amperometry electrochemical analysis. Other electrochemical and optical analyses may be used.

FIG. 1 depicts the correlation between %-bias and an index function based on a ratio parameter (R5/4). The ratio parameter, R5/4, represents the relationship between the currents generated by the analyte in response to the $4^{th}$ and $5^{th}$ pulses of a gated amperometry pulse sequence of FIG. 8C. Other ratio parameters and index functions may be used. Thus, the %-bias of a measured analyte concentration in a biological fluid, such as glucose in whole blood, may be determined from or correlated with the output signals of the analysis, such as the intermediate currents generated by the analyte in response to a gated amperometry sequence.

FIG. 2 depicts the correlation between %-bias and a combination of index functions. The correlation between %-bias and the index function in FIG. 1 may be improved by the linear combination of multiple parameters as shown in FIG. 2. The regression analysis in FIG. 2 has an $R^2$ of 0.8377, which is higher than the $R^2$ of 0.6987 in FIG. 1, thus indicating an improved correlation using multiple parameters (FIG. 2) in comparison to a single parameter (FIG. 1). In FIG. 2, there are two boundaries of ±7 percent and ±10 percent on the %-bias axis, which are projected onto the Index axis. If index values calculated from the intermediate currents are within these boundaries, compensation of the correlations between the measured analyte concentration and the output signals may not be necessary. The boundaries may be determined experimentally, selected based on the one or more parameters used, or chosen using other criteria. Thus, index functions may be used to compensate for part or all of the correlation between the measured analyte concentration and the output signals.

The relationship between %-bias and an index function may be represented as follows:

$$\text{\%-bias} = f(\text{index}) \quad \text{(Equation 1)},$$

where %-bias equals $(\Delta A/A_{ref})*100\%$ and $f(\text{index})$ equals $a_1*\text{Index}+a_0$. $\Delta A$ is the difference between the measured or calculated analyte concentration, $A_{cal}$, and a reference analyte concentration, $A_{ref}$ (a known analyte concentration in a biological sample). Thus, substituting terms for Equation 1 results in the following relationship between %-bias and an index function:

$$(\Delta A/A_{ref})*100\% = a_1*\text{Index}+a_0 \quad \text{(Equation 2)}.$$

Rearranging the terms of Equation 2 results in the following relationship:

$$\Delta A = A_{ref}*(a_1*\text{Index}+a_0)/100 \quad \text{(Equation 3)}.$$

A compensation may be expressed as follows:

$$A_{corr} = A_0 + \Delta A \quad \text{(Equation 4)}.$$

Where $A_{corr}$ is a corrected or compensation analyte compensation and $A_0$ is an initial analyte value from the analysis. While $\Delta A$ may be obtained from Equation 3, $A_{ref}$ in Equation 3 may not be available during the analysis of a biological sample. However, the initial analyte value, $A_0$, may be used from the analysis in place of $A_{ref}$. Thus, Equation 3 may approximated by the following relationship:

$$\Delta A \approx A_0*(a_1*\text{Index}+a)/100 \quad \text{(Equation 5)}.$$

Finally, substituting Equation 5 into Equation 4 results in the following relationship:

$$A_{corr} = A_0 + A_0*(a_1*\text{Index}+a_0)/100 = A_0[1+(a_1*\text{Index}+a_0)/100] \quad \text{(Equation 6)}.$$

From Equation 6, the difference between the measured analyte concentration and a reference analyte concentration, $\Delta A$, is based on an initial analyte value, $A_0$, which may be biased due to one or more errors in the analysis. Thus, there is no reference point or value upon which to base the compensation of the measured analyte concentration.

The %-bias in the correlation of analyte concentrations with output signals also may be represented by one or more slope deviations, $\Delta S$, obtained from one or more error parameters. Error containing portions of output signals are reflected in the deviation between the hypothetical slope of the output signals and the slope of a reference correlation. By determining one or more $\Delta S$ values reflecting this deviation in slope from one or more error parameters, the accuracy and/or precision of an analysis may be increased. One or more $\Delta S$ values for an analysis may be determined from one or more error parameters. The relationship between $\Delta S$ values and the value of one or more error parameters may be described by an index function. Index functions in addition to reference correlation equations may be pre-determined and stored in the biosensor system. Error parameter values may be determined before, during, or after the analysis. Slope-based correction methods may provide a biosensor system the ability to maintain over 95% of the analyses within a ±20% bias limit, more preferably within a ±10% bias limit.

Figure 3:
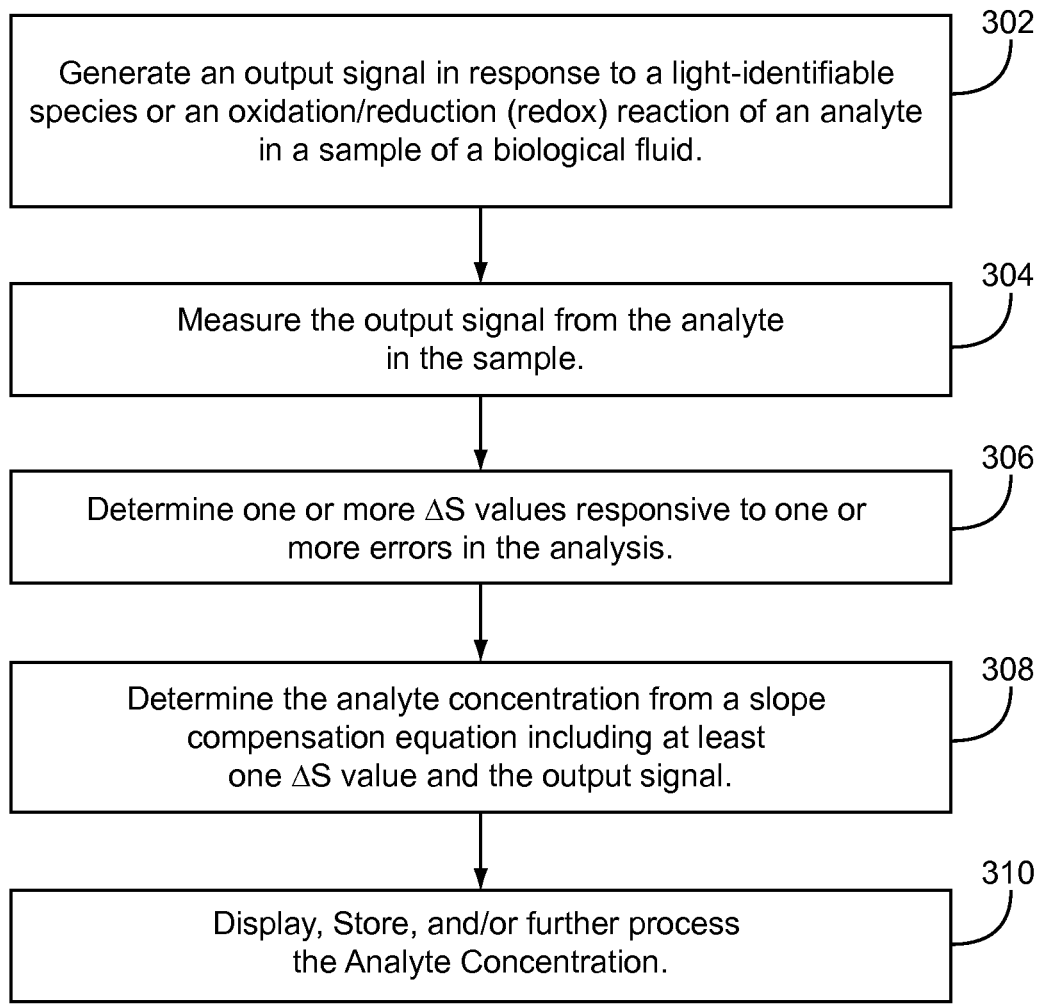
FIG. 3 represents a method for determining an analyte concentration in a sample.

FIG. 3 represents a method for determining an analyte concentration in a sample of a biological fluid. In 302, the biosensor system generates an output signal in response to either a light-identifiable species or an oxidation/reduction (redox) reaction of an analyte in a sample of a biological fluid. In 304, the biosensor system measures the output signal. In 306, one or more ΔS values responsive to one or more errors in the analysis are determined. In 308, the analyte concentration is determined from a slope compensation equation including at least one ΔS value and the output signal. In 310, the analyte concentration may be displayed, stored for future reference, and/or used for additional calculations.

In 302 of FIG. 3, the biosensor system generates an output signal in response to a light-identifiable species or an oxidation/reduction (redox) reaction of an analyte in a sample of a biological fluid. The output signal may be generated using an optical sensor system, an electrochemical sensor system, or the like.

Figure 4:
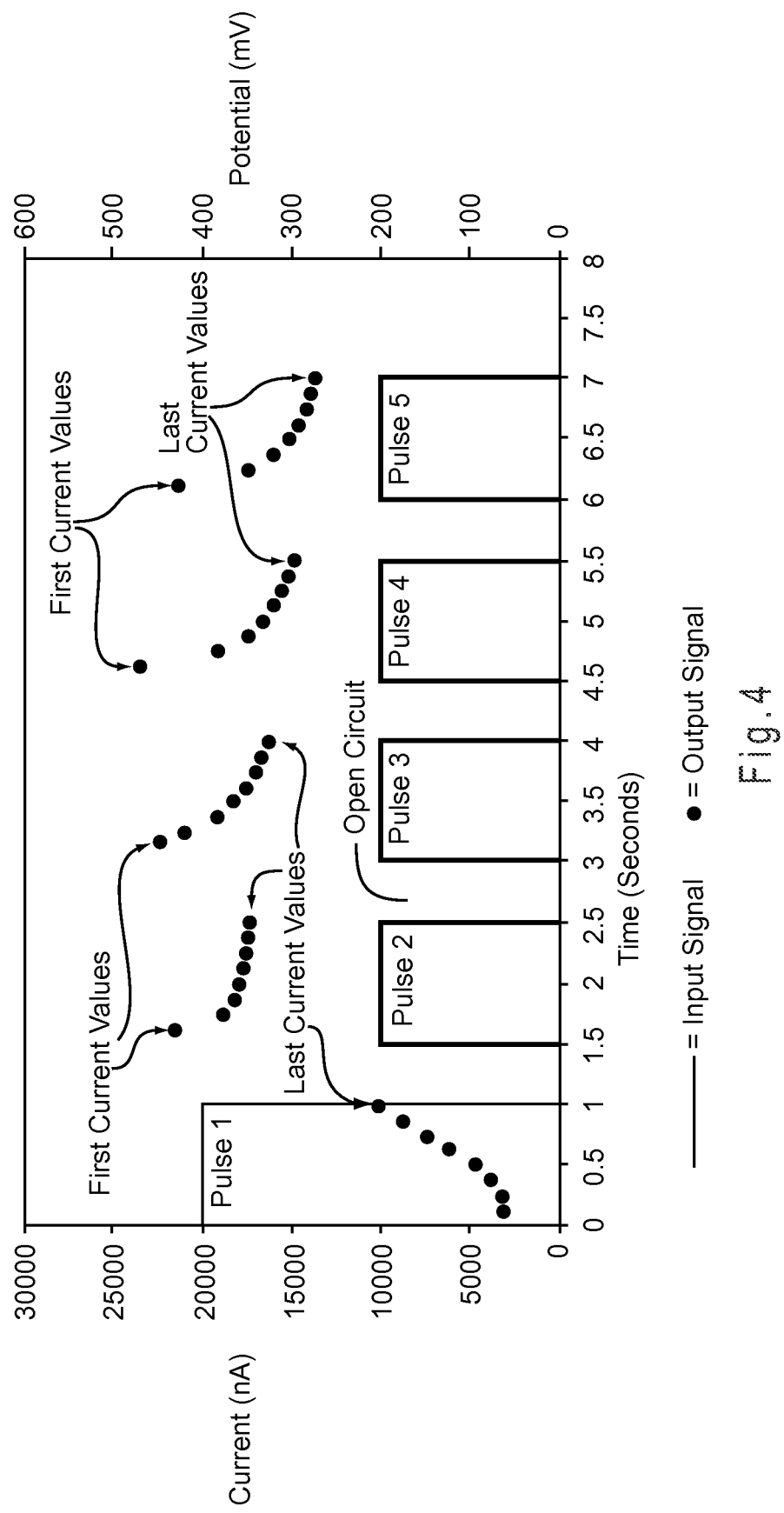
FIG. 4 is a graph illustrating the output signals in relation to the input signals for an electrochemical system using gated amperometry.

FIG. 4 is a graph illustrating the output signals in relation to the input signals for an electrochemical system using gated amperometry. The biosensor system applies a first pulse having a potential of about 400 mV for about 1 sec to the working and counter electrodes. The first pulse is followed by a 0.5 sec relaxation, which may be an essentially open circuit or the like. The output signal or current within the first pulse is measured and may be stored in a memory device. The system may apply a second pulse to the working and counter electrodes at about 200 mV for about 1 sec. The output signal or current within the second pulse is measured and also may be stored in a memory device. The biosensor system continues to apply pulses from the input signal to the working and counter electrodes for the desired time period. The system may measure and store the output signal or current within each pulse. Other input and output signals and other electrochemical systems may be used.

Input signals may be electrical signals, such as current or potential, that pulse or turn on and off in a set sequence. Thus, the input signal is a sequence of excitation pulses separated by relaxations. During a pulse, the electrical signal is present. In gated amperometry, the potential is held relatively constant during a pulse, while in gated voltammetry, the potential varies during a pulse. During a relaxation, the input signal is off. Off includes time periods when an electrical signal is not present and preferably does not include time periods when an electrical signal is present but has essentially no amplitude. The electrical signal may switch between on and off by closing and opening an electrical circuit, respectively. The electrical circuit may be opened and closed mechanically, electrically, or the like.

Input signals may have one or more pulse intervals. A pulse interval is the sum of a pulse and a relaxation. Each pulse has an amplitude and a width. The amplitude indicates the intensity of the potential, the current, or the like of the electrical signal. The amplitude may vary or be substantially constant, such as during amperometry, during the pulse. The pulse width is the time duration of the pulse. The pulse widths in an input signal may vary or be essentially the same. Each relaxation has a relaxation width, which is the time duration of the relaxation. The relaxation widths in an input signal may vary or be substantially the same.

Output signals are currents or potentials generated from the sample that are responsive to the input signal. In amperometric electrochemical systems, the sample may generate the output signal from the redox reaction of the analyte in response to the input signal. Output signals may include those that decline initially, those that increase and then decline, those that reach a steady-state, and those that are transient. For example, the output signal of the first pulse in FIG. 4 increases from the first to the last current value, while the current values from the second through the fifth pulses decrease or decay from the first to last current value. Other types of output signals may be generated.

In 304 of FIG. 3, the biosensor system measures the output signal generated by the analyte in response to the input signal applied to the sample, such as from a redox reaction of the analyte. The system may measure the output signal continuously or intermittently. For example, the biosensor system measured the output signal intermittently during each pulse in FIG. 4, resulting in eight current values during each pulse. The system may show the output signal on a display and/or may store the output signal or portions of the output signal in a memory device.

In 306 of FIG. 3, one or more ΔS values are determined that are responsive to one or more errors. ΔS values may be determined for temperature, hematocrit, and other contributors.

In 308 of FIG. 3, the analyte concentration of the sample is determined from a slope compensation equation including at least one ΔS value and the output signal. The slope compensation equation uses output signal values to provide an analyte concentration. The slope compensation equation compensates for error by adjusting a reference correlation between output signals and the analyte concentrations to provide a compensated or corrected analyte concentration. The slope compensation equation may be represented as follows:

$$A_{corr} = \frac{i - Int}{S_{cal} + \Delta S} \quad \text{(Equation 7)}$$

where $A_{corr}$ is the corrected analyte concentration, i is a value of the output signal from a biosensor system, Int is the intercept from a reference correlation equation, $S_{cal}$ is the slope from the reference correlation equation, and ΔS represents the deviation in slope between $S_{cal}$ and a hypothetical slope of a line ($S_{hyp}$) for the output signal value that provides an analyte concentration of the sample without error. The Int and $S_{cal}$ values for the reference correlation equation may be implemented as a program number assignment (PNA) table, another look-up table, or the like in the biosensor system. Other slope compensation equations including at least one ΔS value and the output signal may be used.

In Equation 7, an index function, f(index), may be substituted for ΔS. While the index function, f(index), has a general form of $b_1$*Index+$b_0$, other index functions may be used. Thus, Equation 7 may be rewritten as follows:

$$A_{corr} = \frac{i - Int}{S_{cal} + \Delta S} \quad \text{(Equation 8)}$$
$$= \frac{i - Int}{S_{cal} + f(\text{Index})}$$
$$= \frac{i - Int}{S_{cal} + b_1 * \text{Index} + b_0}.$$

A comparison of Equation 8 with Equations 5 and 6 shows the improvement from using the slope deviation to represent the %-bias. The compensation of the analyte concentration in Equations 5 and 6 is based on a predetermined analyte concentration $A_0$. In contrast, the compensation of the analyte concentration in Equation 8 is responsive to adjusting the correlation slope through the terms in the denominator. Additionally, there is no reference value or reference point incorporated with the compensation of the analyte concentration from Equations 5 and 6. $A_{ref}$ is approximated by $A_0$. In Equation 8, the slope $S_{cal}$ is incorporated with the compensation of the analyte concentration and may be stored in a device implementing the compensation system. There is no approximation of $S_{cal}$ during the calculation of the analyte concentration. Thus, the compensation of analyte concentration from Equation 8 may be more accurate than the compensation of analyte concentration from Equations 5 and 6.

Equation 7 is a representation of the corrected analyte concentration determined using the slope deviation $\Delta S$, where $\Delta S$ is essentially the total slope deviation related to essentially the total error associated with the analyte analysis. The total slope deviation may be caused by one or more error sources. Equation 7 may be used with any signal having a substantially linear response to analyte concentration. Thus, the output signal preferably has a linear relationship with the analyte concentration in the sample and may originate from a redox reaction, light-identifiable species, or other process. The reference correlation equation describes a function relating the output signals from a biosensor system to analyte concentration values determined from a reference instrument. For example, the output signal from a biosensor system for a specific sample may be related to the analyte concentration values determined from a YSI reference instrument for the same sample. Equation 7 may be used with other signals, such as signals that are near or partially linear.

$\Delta S$ is responsive to one or more errors in the output signal $i$ and represents the error containing portions of the output signal not responsive to the analyte concentration of the sample. Thus, $S_{hyp}=S_{cal}+\Delta S$. One or more values for Int and $S_{cal}$ may be stored in the biosensor system for comparison with the output signal $i$ to determine $A_{corr}$ for the sample. One or more $\Delta S$ values are determined during the analysis from one or more index or like functions.

Figure 5:
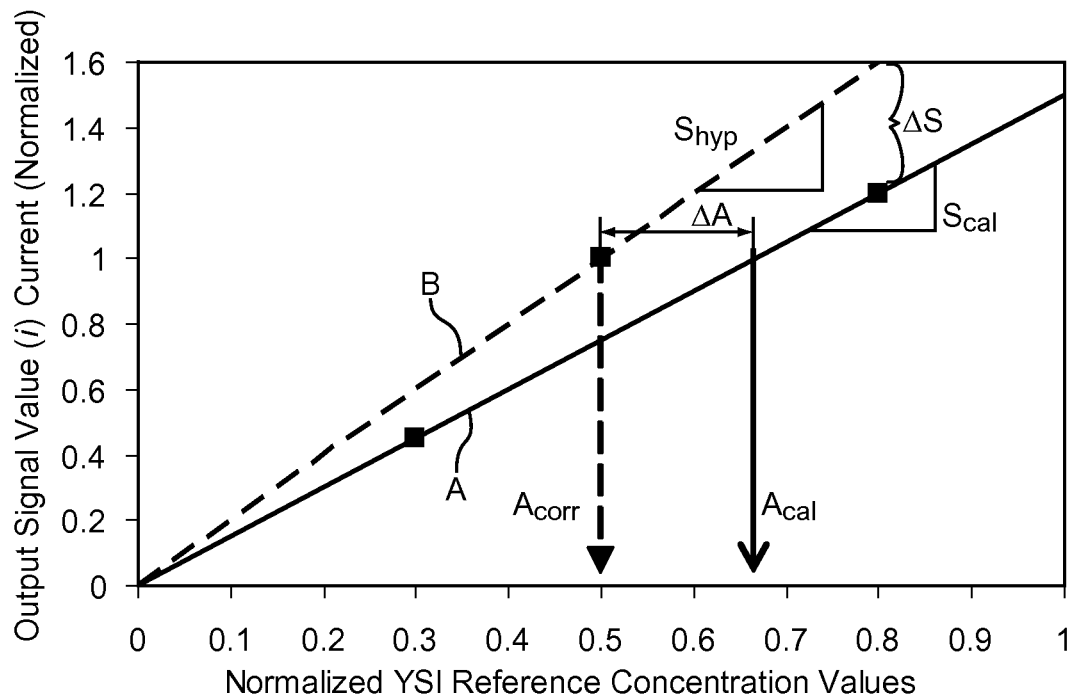
FIG. 5 depicts the relationship between $S_{cal}$, $S_{hyp}$, ΔS, $A_{corr}$, $A_{cal}$, and ΔA.

FIG. 5 shows the relationship between $S_{cal}$, $S_{hyp}$, $\Delta S$, $A_{corr}$, $A_{cal}$, and $\Delta A$. Line A represents a reference correlation having a slope $S_{cal}$ and relating an output signal in the form of current values from a biosensor system to analyte concentration values obtained from a YSI or other reference instrument for the samples. When used during the analysis of a sample by a biosensor system, the reference correlation of Line A may include one or more errors that may provide an inaccurate and/or imprecise analyte concentration value. Line B represents an error-compensated correlation having a slope $S_{hyp}$ and relating current values obtained from the system with the sample analyte concentration values as obtained from the reference instrument. The error-compensated correlation has been adjusted or modified to reduce or substantially eliminate the one or more errors. $\Delta S$ is the difference in slope between these correlation lines. $\Delta A$ is the difference between the uncompensated or uncorrected ($A_{cal}$) and error compensated or corrected ($A_{corr}$) determined analyte concentration values.

Without compensation or correction, a specific output signal value will provide a different sample analyte concentration from the $S_{cal}$ reference correlation line than from the $S_{hyp}$ error-compensated line. The $A_{corr}$ value obtained from the $S_{hyp}$ error-compensated line provides a more accurate value of the analyte concentration in the sample. Thus, Equation 1 translates a current value, $S_{cal}$, and Int into the compensated analyte concentration value $A_{corr}$ using $\Delta S$. In this way, the percent bias may be linked through $\Delta S$ into Equation 7. The percent bias values may be pulled toward the center of a bias distribution through the linkage of $\Delta S$ to the percent bias. As $\Delta S$ is responsive to bias, changing $\Delta S$ affects the amount of bias remaining in the compensated analyte concentration of the sample.

In 310 of FIG. 3, the analyte concentration value may be displayed, stored for future reference, and/or used for additional calculations.

The responsiveness of $\Delta S$ to one or more errors may be represented by an index function. To determine one or more index functions, the deviation in the slope of the correlation equation in response to the one or more errors ($\Delta S_{cal}$) may be determined from experimental data, such as during factory calibration, as follows:

$$\Delta S_{cal} = \frac{i - Int}{A_{ref}} - S_{cal} \qquad \text{(Equation 9)}$$

where $i$ is a value of the output signal from a biosensor system, Int is the intercept from a reference correlation equation, $A_{ref}$ is the reference analyte concentration of the sample, such as obtained from a reference instrument, and $S_{cal}$ is the slope from a reference correlation equation, such as $i=S_{cal}*A_{ref}+Int$. One or more $\Delta S_{cal}$ values may be determined from different system output signals at each reference analyte concentration. In this manner, for multiple known analyte concentrations, an output signal value may be obtained from the biosensor system and a corresponding $\Delta S_{cal}$ value determined. An initial index function may be determined by taking the $\Delta S_{cal}$ values from Equation 9 and correlating them to an error parameter.

Index functions compensate the measured analyte concentration for one or more errors in the analyte concentration analysis. One or more index functions may be used. An index function that correlates with the total slope deviation $\Delta S$ would provide an ultimate total error compensation of the analyte concentration since this index function could be used to compensate for the total error in the analysis without having to know the exact cause of the slope deviation $\Delta S$ and thus the bias of the measured analyte concentration. An index function may be responsive to an error parameter, such as temperature, which is measurable by another means. An index function may be a calculated number that correlates with an error parameter such as hematocrit and represents the influence of this error parameter on the slope deviation $\Delta S$. Thus, error parameters may be any value responsive to one or more errors in the output signal and may be measured, calculated, or determined through other means. Index functions may be experimentally determined as a regression equation of the plot between $\Delta S_{cal}$ and an error parameter.

Other methods may be correlated with error parameters, such as the %-hematocrit level of whole blood samples. For example, U.S. Pat. No. 7,338,639 describes using AC phase angle measurements to determine the hematocrit level and temperature errors associated with whole blood samples. EP 1,742,045 A1 describes the determination of the hematocrit by an independent electrode and the correlation of the hematocrit level with output currents. Thus, the output signals of these methods may be used to compose the index functions. However, these methods may be more complex to implement than using the correlation with the slope deviation $\Delta S$ as discussed. The correlation with the slope deviation $\Delta S$ may be implemented using the intermediate DC signals of gated amperometry, which does not require more than two electrodes to generate the output signals for determining the hematocrit compensation. In addition, the intermediate DC signals of gated amperometry do not require any complicated AC circuitry to excite and generate the output signals to determine the hematocrit compensation. The use of gated amperometry translates into equipment and thus cost savings of electronic device used to implement the analyte compensation system.

Figure 6:
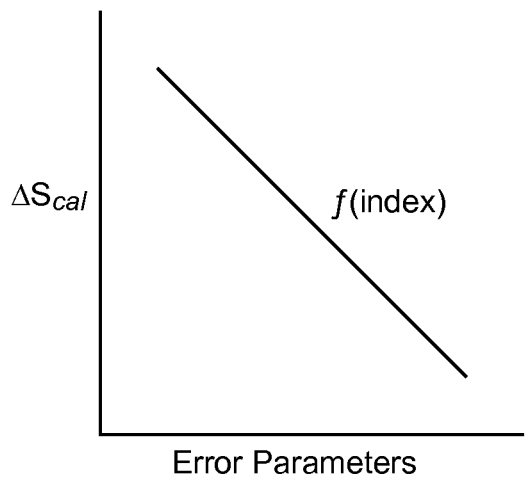
FIG. 6 depicts a linear index function f(Index) relating $ΔS_{cal}$ to error parameters.

FIG. 6 shows a linear index function f(Index) relating $\Delta S_{cal}$ to error parameters. Error parameters are the causes of errors in the analyte concentration analysis. Error parameters include temperature, hematocrit level, and the like as discussed. Index functions compensate the measured analyte concentration for one or more error parameters or errors in the analysis as discussed. Index functions may be calculated using part or all of output signals such as currents, AC phase angle signals, and the like. Thus, the error parameters and the $\Delta S_{cal}$ values determined from Equation 9 may be used to determine one or more index function f(Index). As $\Delta S$ represents the difference between the $S_{hyp}$ for the analyte concentration in a sample determined from the output signal and the $S_{cal}$ obtained from a reference correlation equation for a specific output signal, the f(Index) function represents a relationship between $\Delta S$ and one or more error parameters. Index functions may be determined for any factor describing a portion of the output signal attributed to error.

A linear index function may be determined as follows:

$$f(\text{Index}) = a \cdot \text{Error Parameter} + b \quad \text{(Equation 10)}$$

where a and b are pre-determined values for the slope and intercept, respectively, of the index function and one or more Error Parameter is determined from the analysis of a sample by the biosensor system. For a linear index function, the values of a and b may be taken from any line correlating the $\Delta S_{cal}$ values with the error parameters. The index function f(Index) also may be described with a near linear or polynomial equation. Linear and second order polynomial equations may be used to describe index functions. Index functions may be pre-determined for multiple error parameters and stored in the biosensor system. For example, the a and b values of a linear index function may be implemented as a program number assignment (PNA) table, another look-up table, or the like in the biosensor system. Other index functions may be used.

Temperature may be considered an error parameter for the analysis because an error in concentration values may arise from performing an analysis at a temperature other than that at which the reference correlation was determined. For example, temperature affects the oxidation and diffusion of glucose in a sample of whole blood and the diffusion of optically active molecules. The temperature for the analysis may be determined from any source, such as a thermocouple, calculated estimates, and the like.

Figure 7A:
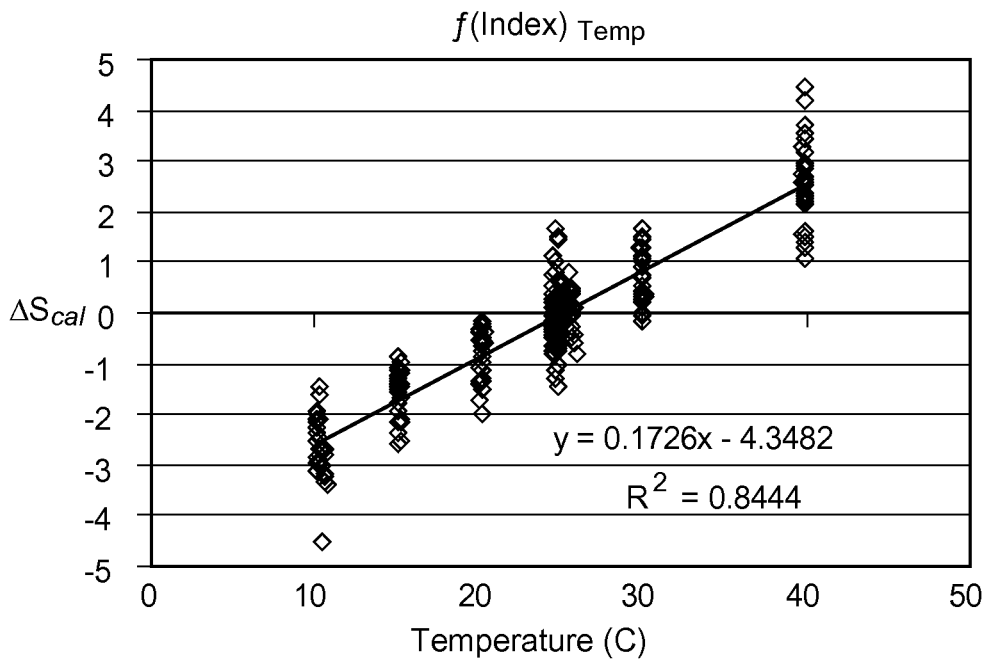
FIG. 7A plots output signal values recorded at multiple temperatures against $ΔS_{cal}$ values.

FIG. 7A plots $\Delta S_{cal}$ values determined from output signal values recorded as a function of temperature with Equation 9 at 10, 15, 20, 25, 30, and 40° C. The resulting line showed a $R^2 = 0.8444$ correlation and provided an index function for temperature compensation, $f(\text{Index})_{Temp}$. In this instance, $f(\text{Index})_{Temp}$ relates temperature to the deviation in slope between the reference correlation slope determined at a reference temperature and the hypothetical slope of the line that would provide the temperature affected analyte concentration at the temperature at which the analysis was performed. The index function for temperature $f(\text{Index})_{Temp}$ may be stored in the biosensor system with the reference correlation equation.

Figure 7B:
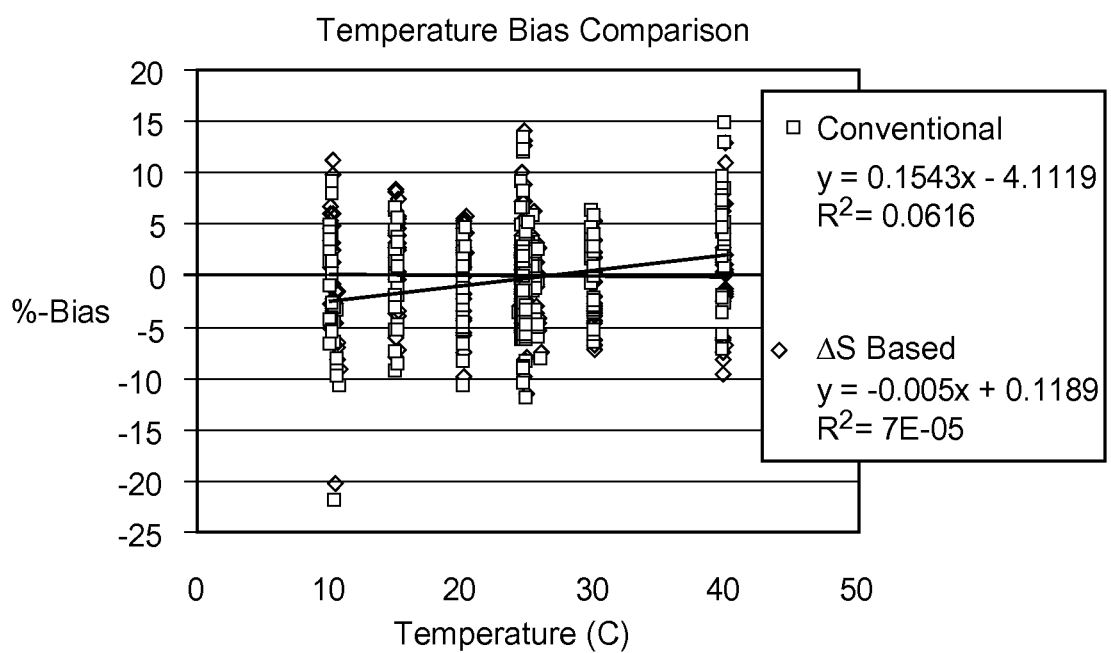
FIG. 7B depicts an improvement in percent bias values from slope-based compensation.
Figure 7C:
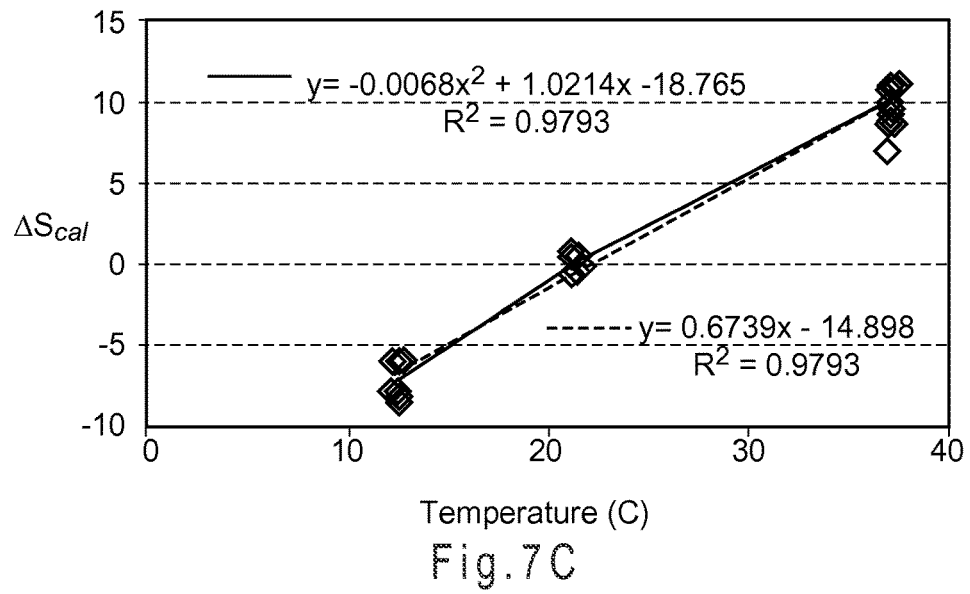
FIG. 7C depicts linear and $2^{nd}$ order polynomial equations as f(Index)Temp relating temperature to $ΔS_{cal}$.
Figure 7D:
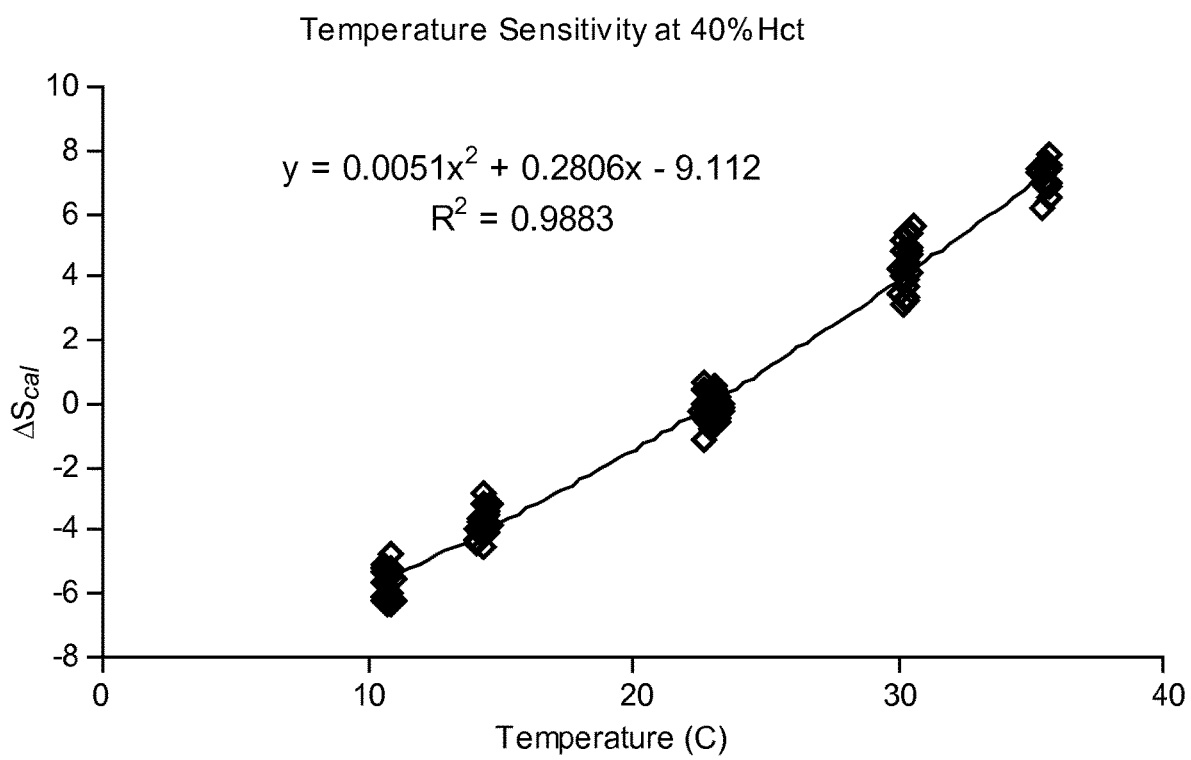
FIG. 7D represents the temperature sensitivity of $ΔS_{cal}$ vs. temperature for another sensor type.

FIG. 7B shows the improvement in percent bias values from the method of FIG. 3 using the f(Index)Temp index function derived from FIG. 7A and a conventional method using the concurrent alteration of slope and intercept values. The method of FIG. 3 reduced temperature bias in relation to the conventional method, as shown by the slope correlation decrease from 0.1543 to −0.005, where larger numerical slope values signify an increased relationship between temperature and percent bias. In addition to linear index functions, such as from FIG. 7A, polynomial equations may be used to describe the relationship between error parameters and $\Delta S_{cal}$ values. FIG. 7C shows linear and $2^{nd}$ order polynomial equations as $f(\text{Index})_{Temp}$ relating $\Delta S_{cal}$ to temperature. In this instance the $R^2$ correlation showed a slight improvement for the polynomial equation; however, index functions relating other error parameters to $\Delta S_{cal}$ may show larger differences between linear and polynomial equations. FIG. 7D represents the temperature sensitivity of $\Delta S_{cal}$ vs. temperature for another sensor type. The data generated from 40% hematocrit whole blood samples fits a second order polynomial. Thus, temperature is an error parameter, which caused the slope deviation $\Delta S$.

In addition to a single f(Index) function, $\Delta S$ may be represented by a combination of f(Index) functions, where $\Delta S$ is conceptually represented as follows:

$$\Delta S = f(\text{Index})_1 + f(\text{Index})_2 + f(\text{Index})_3 + \quad \text{(Equation 11)}$$

where each $f(\text{Index})_n$ describes a different portion of the slope deviation $\Delta S$ arising from different errors present in the output signal. Depending on the analysis, it may be preferred to describe $\Delta S$ with multiple index functions describing different error parameters. Preferably, when represented by $f(\text{Index})_n$, the different error parameters are independent of each other. Independent relationships between the different error sources as expressed in f(Index) functions may provide independent compensation for each error source, thus providing a more accurate determination of the analyte concentration of the sample. For example, when errors arising from temperature and hematocrit are substantially unrelated when expressed as f(Index) functions, $f(\text{Index})_1$ may describe temperature error and $f(\text{Index})_2$ may describe hematocrit error. Other error sources substantially unrelated to temperature or hematocrit may be represented by $f(\text{Index})_3$ and the like. While index functions from substantially unrelated error sources are preferred, other index functions may be used.

The compensation or correction of the analyte concentration value may be started with the error parameter accounting for the largest error in the output signal. After compensating for the largest effect, any error remaining in $\Delta S$ may be compensated or corrected with additional error parameters independent of the parameter responsive to the largest error, as previously described. After an initial index function is determined, such as $f(\text{Index})_{Temp}$, subsequent index functions may be determined from additional error parameters and $\Delta S_{2cal}$ values determined from an equation as follows:

$$\Delta S_{2cal} = S_{cal} * \left( \frac{A_{corr(1)}}{A_{ref}} - 1 \right) \quad \text{(Equation 12)}$$

where $\Delta S_{2cal}$ is slope deviation remaining after the first $f(\text{Index})_1$ compensation and represents the difference in slope between $S_{cal}$ and $S_{hyp}$ for a second error parameter after the first compensation, $S_{cal}$ is the slope from the reference correlation equation, $A_{corr(1)}$ is the analyte concentration corrected with $f(\text{Index})_1$, such as temperature, and $A_{ref}$ is the reference analyte concentration of the sample, such as determined with a reference instrument. Additional index functions may be determined after a second $A_{corr(2)}$ is determined by taking into account the first and second index functions. These and other index functions may be stored in the biosensor system as a PNA table, another look-up table, or the like. As successive $A_{corr}$ values are determined using additional index functions, the bias in the determined concentration values may decrease until the bias level approaches the random noise level of the analysis. Other equations to determine $\Delta S_{2cal}$ values from a first index function and second error parameters may be used.

The error in concentration values arising from the hematocrit and other effects may be described by multiple parameters responsive to the error, such as output signal values other than that used to determine the analyte concentration of the analyte, ratios of output signal values, mathematical combinations of output signal values, and other values derived from the output signal and/or other sources. These error parameters may be internal to the intermediate values of the output signal or derived from the intermediate values of the output signal. To determine $f(Index)_{Hct}$, for example, the $\Delta S_{2cal}$ values determined from Equation 12 at a specific output signal value may be plotted on the Y-axis of FIG. 6, and error parameter values corresponding to the specific output signal value and responsive to hematocrit bias may be plotted on the X-axis. The resulting correlation would be $f(Index)_{Hct}$ based on the hematocrit responsive error parameter.

When multiple index functions are used to describe $\Delta S$, the corrected analyte concentration may be calculated using an equation represented as follows:

$$A_{corr(2)} = \frac{i - Int}{S_{cal} + \Delta S_1 + \Delta S_2} \quad \text{(Equation 13)}$$

where $A_{corr(2)}$ is the analyte concentration corrected with two $\Delta S$ values, i is a value of the output signal including multiple sources of error from different contributors, Int is the intercept from a reference correlation equation, $S_{cal}$ is the slope from the reference correlation equation, and $\Delta S_1$ and $\Delta S_2$ represent the deviation in slope attributable to two error contributors. Other equations to determine a corrected analyte concentration from multiple index functions may be used.

Figure 8A:
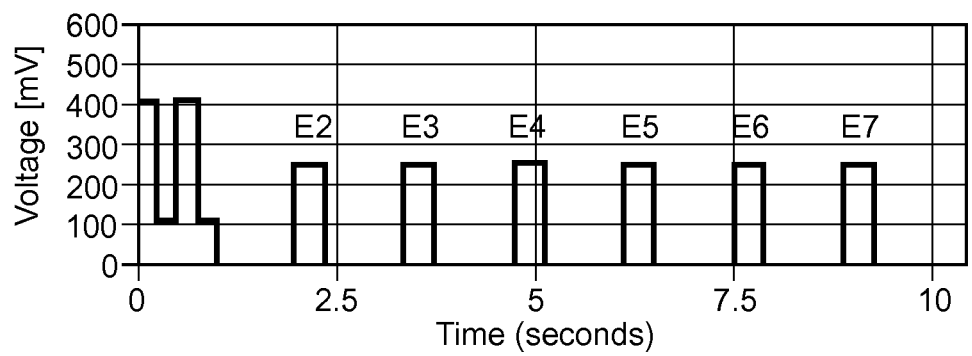
FIG. 8A depicts a gated pulse sequence where the input signal includes multiple excitations and relaxations.
Figure 8B:
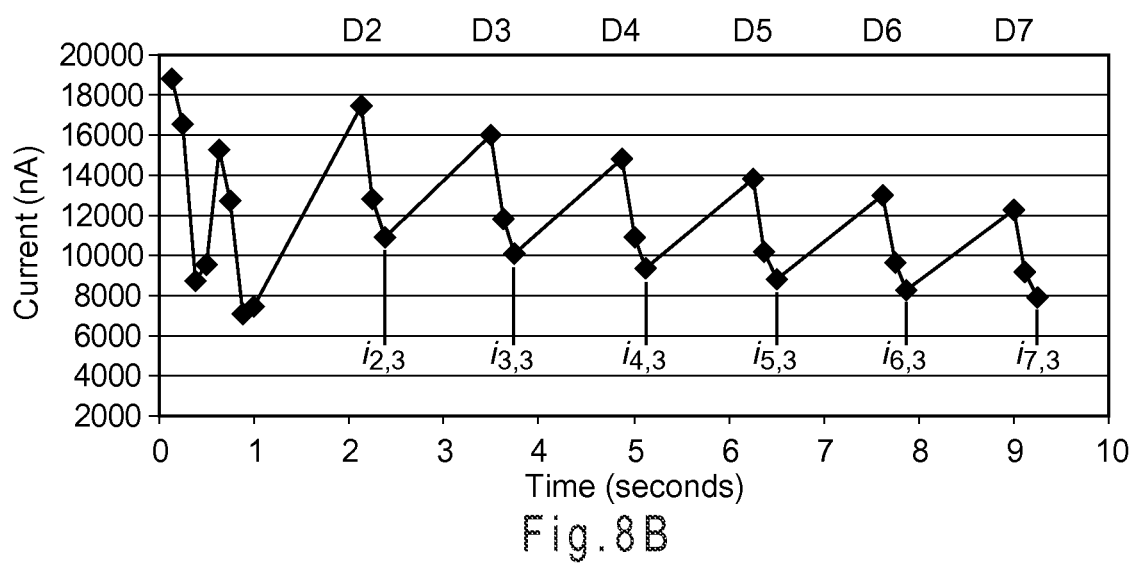
FIG. 8B depicts the output signal currents from the input signals.

While many techniques may be used to determine error parameters responsive to a bias contributor, output signal values are preferred to describe some types of bias contributors, such as hematocrit error. FIG. 8A depicts a gated pulse sequence where the input signal includes multiple excitations and relaxations, and excitations E2-E7 are labeled. FIG. 8B depicts the output signal currents from the input signals labeled as current decays D2-D7. The first number in the subscript of the i values denote the excitation number, while the second number in the subscript denotes the output signal value of the decay being described. For example, $i_{2,3}$ denotes the third current value recorded for D2.

Multiple output signal values may be combined to determine error parameters of varying complexity. Table I below, shows multiple error parameters and the corresponding output signal values from FIG. 8B.

TABLE I

| Error Parameter | Output Signal Values |
| --- | --- |
| R2 | $i_{2,3}/i_{2,1}$ |
| R3 | $i_{3,3}/i_{3,1}$ |
| R4 | $i_{4,3}/i_{4,1}$ |
| R5 | $i_{5,3}/i_{5,1}$ |
| R2/R3 | $(i_{2,3}/i_{2,1})/(i_{3,3}/i_{3,1})$ |
| R4/3 | $i_{4,3}/i_{3,3}$ |
| R5/4 | $i_{4,3}/i_{4,3}$ |
| R6/5 | $i_{6,3}/i_{5,3}$ |
| Index-I | R4/3 − (R2/R3) |
| Index-II | $(R4/3)^p - (R2/R3)^q$ where p and q are positive and may or may not be equal |

Figure 8C:
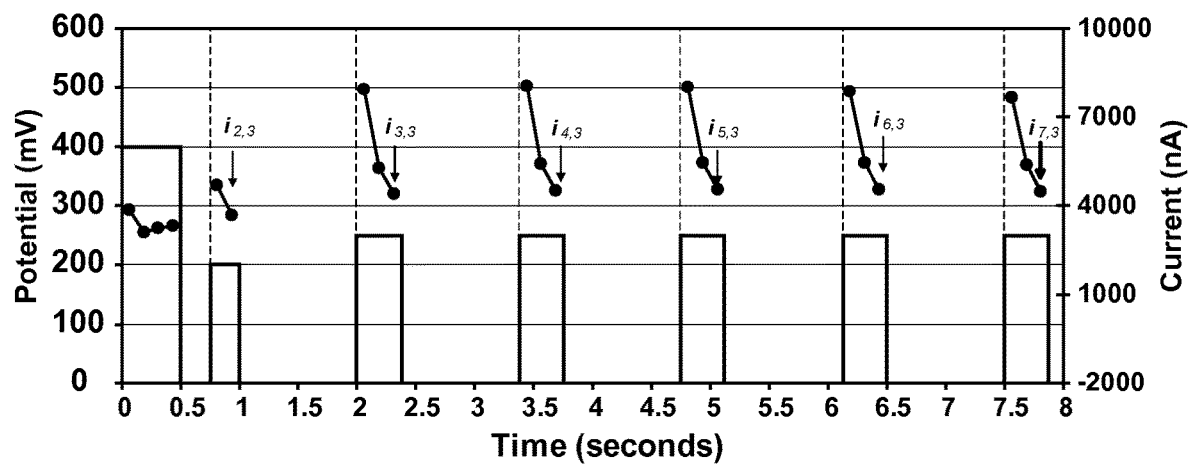
FIG. 8C depicts another gated pulse sequence where the input signal includes multiple excitations and relaxations using gated amperometry.
Figure 8D:
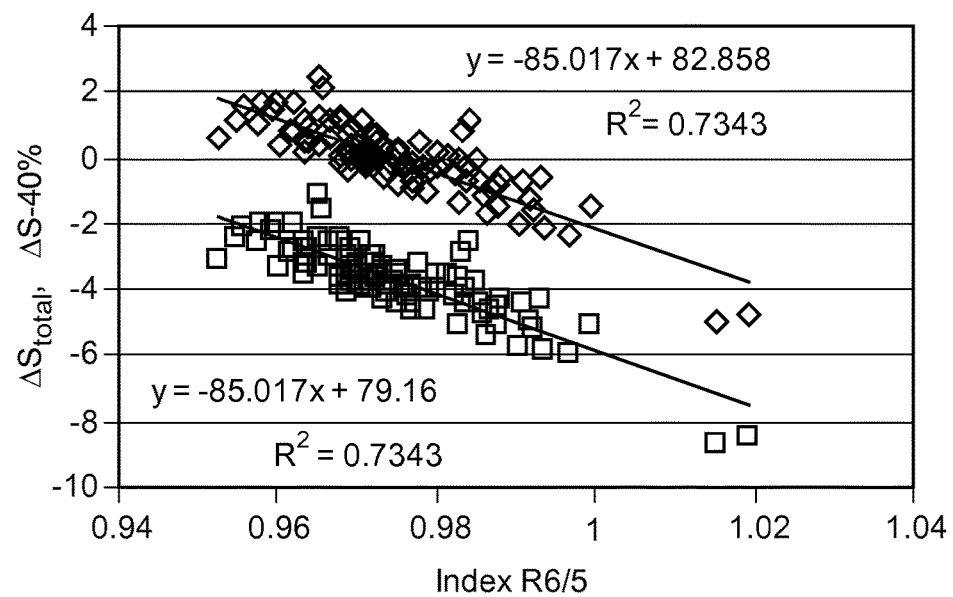
FIG. 8D depicts the correlation between the $ΔS_{total}$ and ΔS-40% against a common index R6/5 with respect to the current labels in FIG. 8C.
Figure 8E:
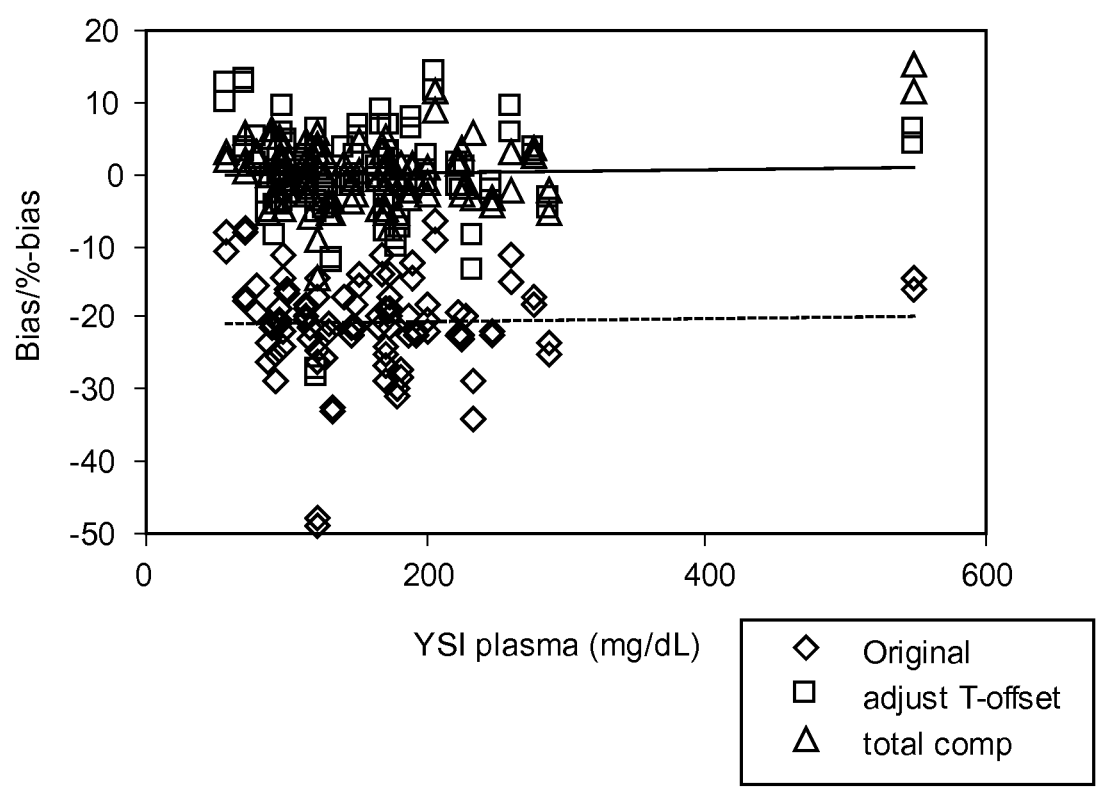
FIG. 8E plots the bias/%-bias before and after compensation.
Figure 9A:
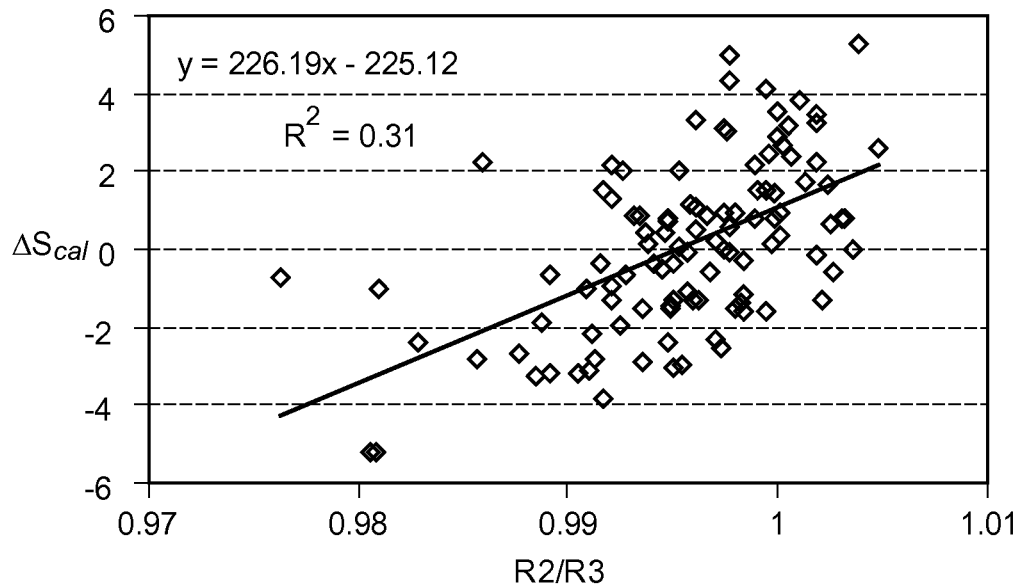
FIGS. 9A-9D depict the correlations between $ΔS_{cal}$ and the error parameters of R2/R3, R4/3, Index-I, and Index-II, respectively, for a biosensor system.
Figure 9B:
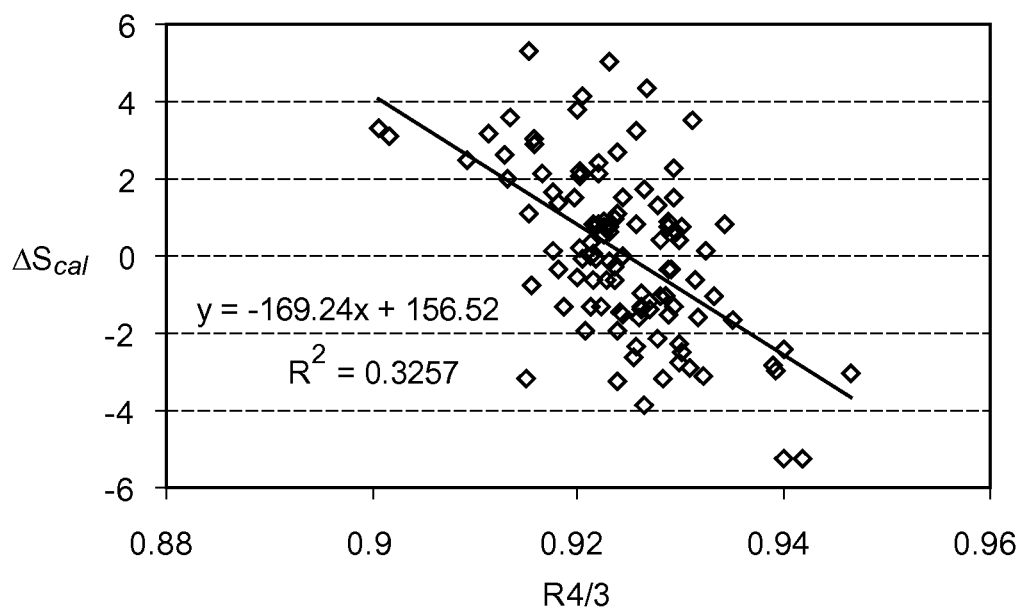
Figure 9C:
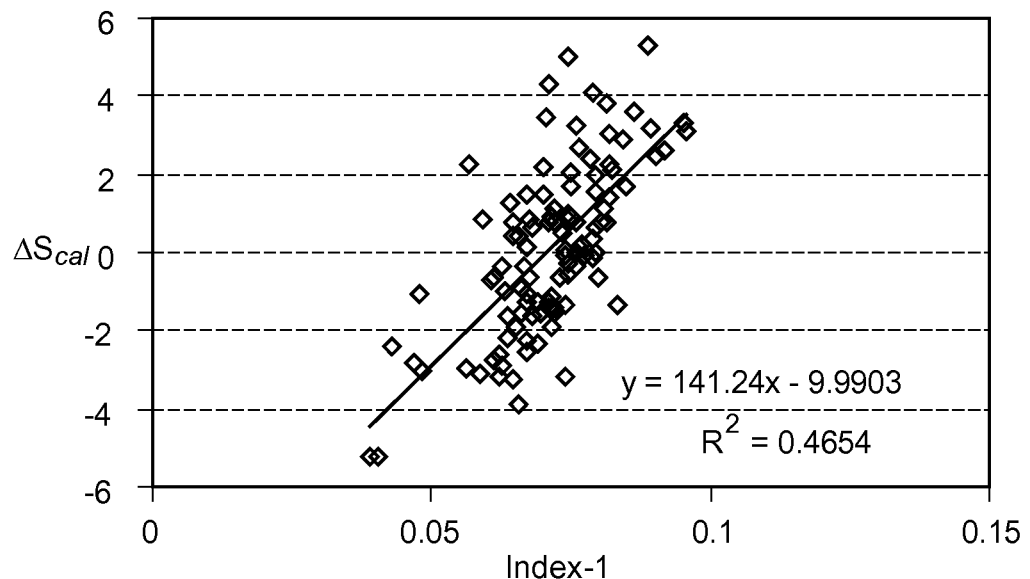
Figure 9D:
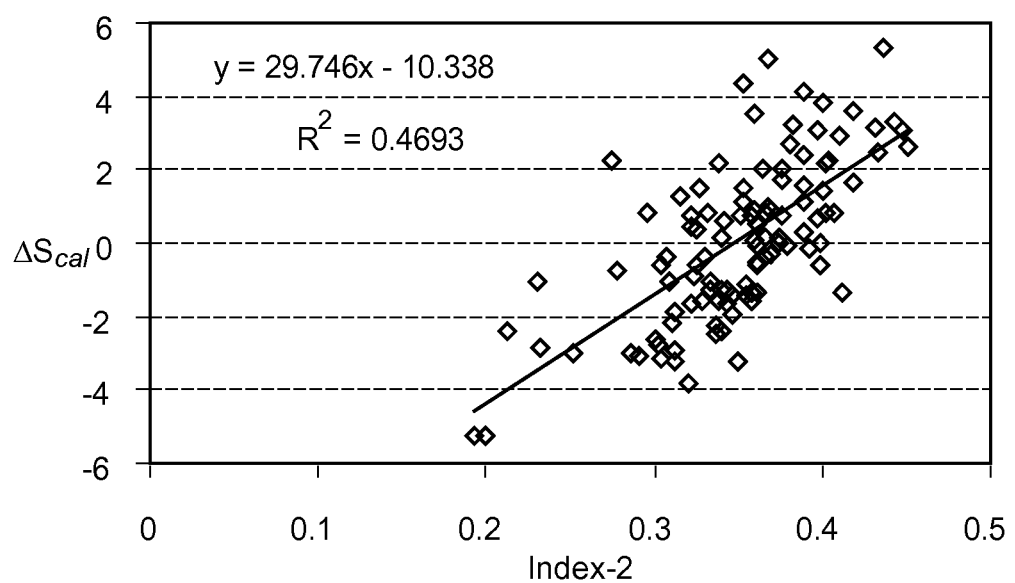

An example of using one-step to compensate for more than one error parameter is provided in reference to FIGS. 8C-8D is given here. FIG. 8C depicts another gated pulse sequence where the input signal includes multiple excitations and relaxations using gated amperometry. The potential sequence is slightly different from that illustrated in FIG. 8A in that the first pulse in FIG. 8C is split into two pulses. The timing of the following pulses is the same as in FIG. 8A. Thus, the labeling of currents and the simple ratio indices differ by one number. For instance, the ratio R4/3 for FIG. 8C is equivalent to the ratio R3/2 for FIG. 8A, as well as the ratio R5/4 for FIG. 8C is equivalent to the ratio R4/3 for FIG. 8A, etc. A study was conducted with the capillary blood samples tested at room temperature and the venous samples tested at a lower temperature of average 15.7° C. from about 50 donors. In FIG. 8D, the $\Delta S_{total}$ and ΔS-40% (representing adjusting temperature offset to $\Delta S$) are plotted against the common index R6/5 with respect to the current labels in FIG. 8C. The open squares represent $\Delta S_{total}$. The open diamonds represent the one after adjusting the temperature offset to $\Delta S_{total}$. The two plots differ only in the regression intercept, with both having essentially the same slope. This difference in intercept of the $\Delta S$ vs. R6/5 plots represents the average temperature effect on the entire data population. If the regression equation from $\Delta S_{total}$ vs. R6/5 is substituted into Equation 7, glucose readings are compensated for both the temperature and hematocrit. FIG. 8E shows the plots of bias/%-bias before and after compensation. The open diamonds represent the population of the original data, with a mean bias of −21 and a standard deviation (SD value) of 6.75. The open triangles represent the population after total error compensation, with a mean bias of −0.08 and a standard deviation of 4.32. The reduction in mean %-bias is the removal of temperature effect on the data population. The reduction in SD value represents reducing the bias spread, thus increasing the accuracy.

FIGS. 9A-9D show the correlations between $\Delta S_{cal}$ and the error parameters of R2/R3, R4/3, Index-I, and Index-II, respectively, for a biosensor system. About 100 samples from 50 subjects (2 samples per subject) containing glucose as an analyte at various concentrations were used. For Index-II, the integer value of six was chosen for p and q. Each figure includes the regression equation representing the index function that could be used to determine $\Delta S$ values from the associated error parameter for use in Equation 7. The larger the $R^2$ value for the correlation, the more responsive the error parameter is to the bias. Of the error parameters attempted, Index-II was most responsive to bias due to the greatest $R^2$ value. Thus, if Index-II was to be used as an index function to determine $\Delta S$ for the analysis, the f(Index) equation y=29.746x−10.338 could be used, where x is the value of the Index-II error parameter from the analysis and y is the value determined for $\Delta S$.

Figure 10A:
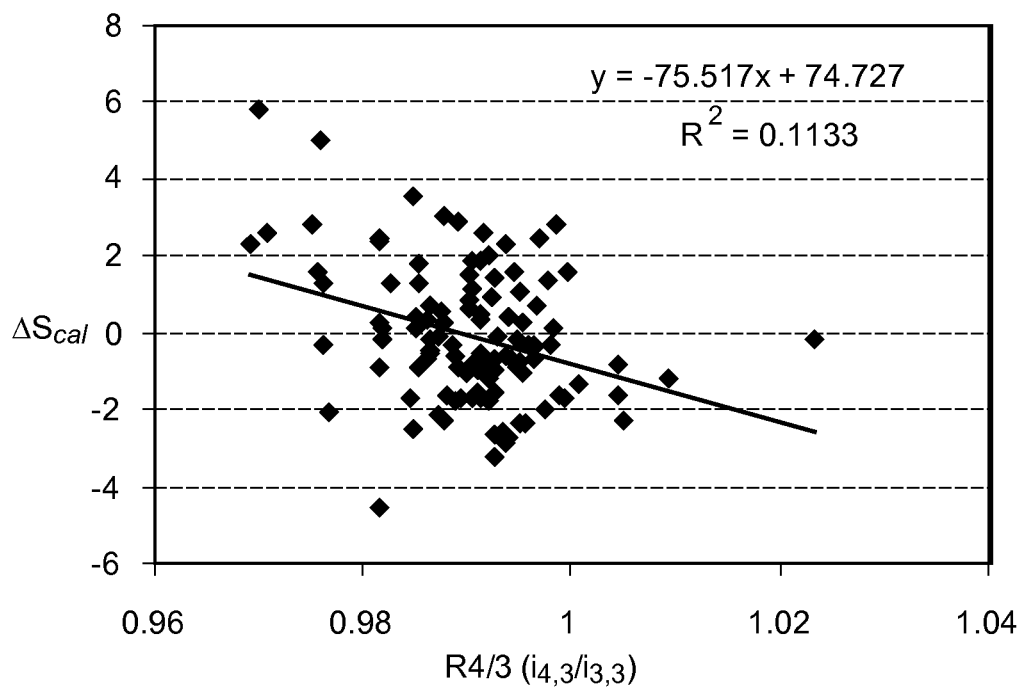
FIGS. 10A-10C depict the correlations between $ΔS_{cal}$ and the error parameters of R4/3, R5/4, and R6/5, respectively, for a biosensor system using different reagents to react with the analyte in the sample.
Figure 10B:
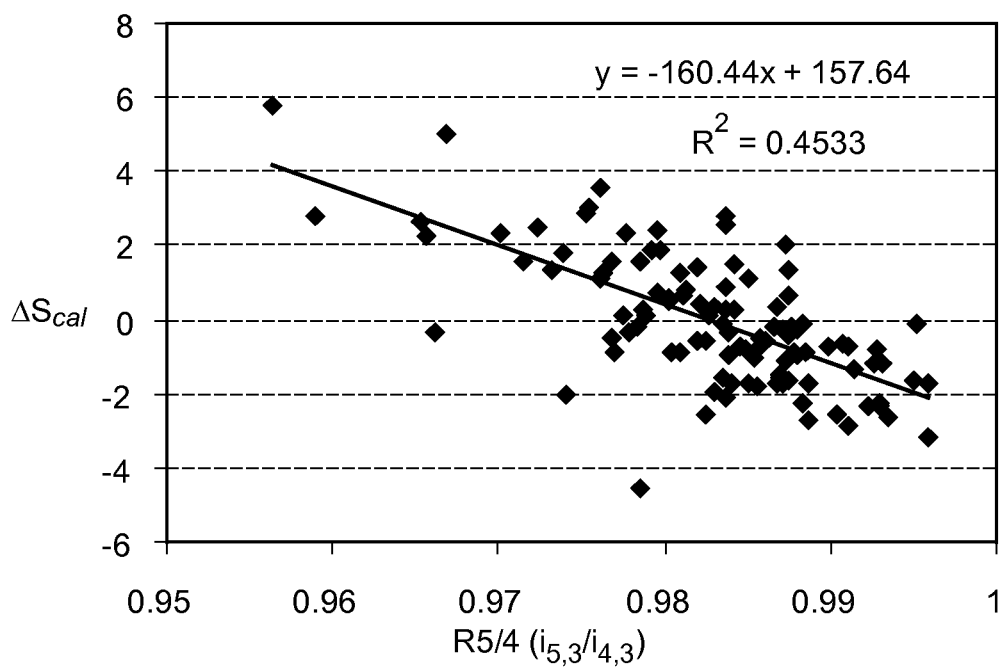
Figure 10C:
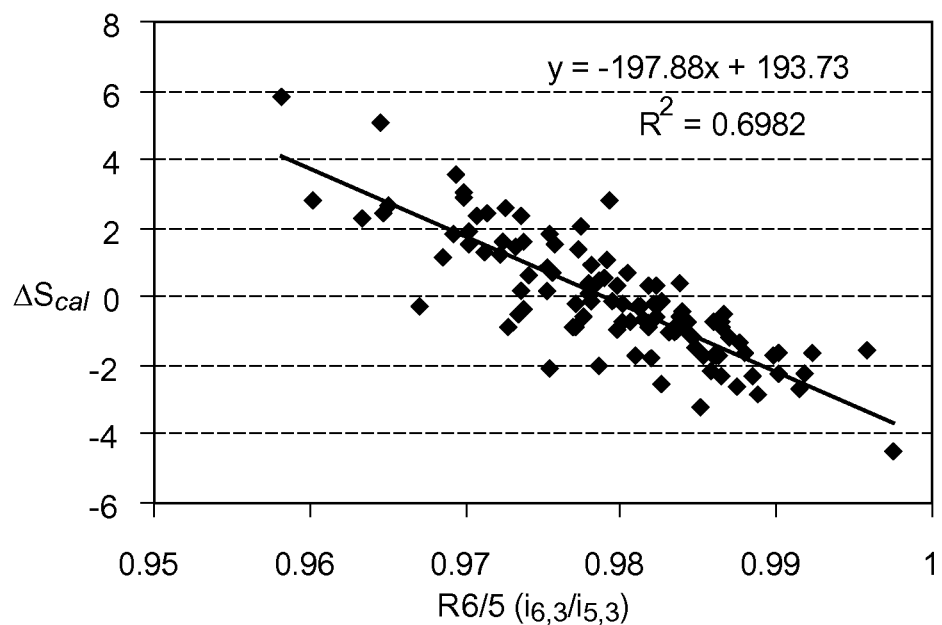

FIGS. 10A-10C show the correlations between $\Delta S_{cal}$ and the error parameters of R4/3, R5/4, and R6/5, respectively, for a biosensor system using different reagents than in FIG. 9. The glucose concentrations determined from about 100 whole blood samples were used. Values for $\Delta S_{cal}$ representing total bias error, as could be determined from Equation 9, were used. The $R^2$ values for R4/3, R5/4, and R6/5 were 0.1133, 0.4533, and 0.6982, respectively, showing that R6/5 was most responsive to the error. As the $R^2$ values increased from 0.1133 to 0.4533, and finally to 0.6982, the percent of the determined analyte concentration values within a ±10% bias limit increased from 79.6%, to 89.8%, and finally reaching 95.4% when using the R6/5 error parameter to determine $\Delta S_{cal}$. Each of the error parameters when used to determine $\Delta S$ values for Equation 7 successfully reduced the percent bias spread of the determined analyte concentrations by pulling the bias toward the center of the distribution. Thus, $\Delta S$ values determined from error parameters increased the number of analyte concentration values falling within a ±10% bias limit from 75.5% (uncompensated) to 95.4% (compensated with R6/5), a 20% improvement in accuracy.

Figure 11A:
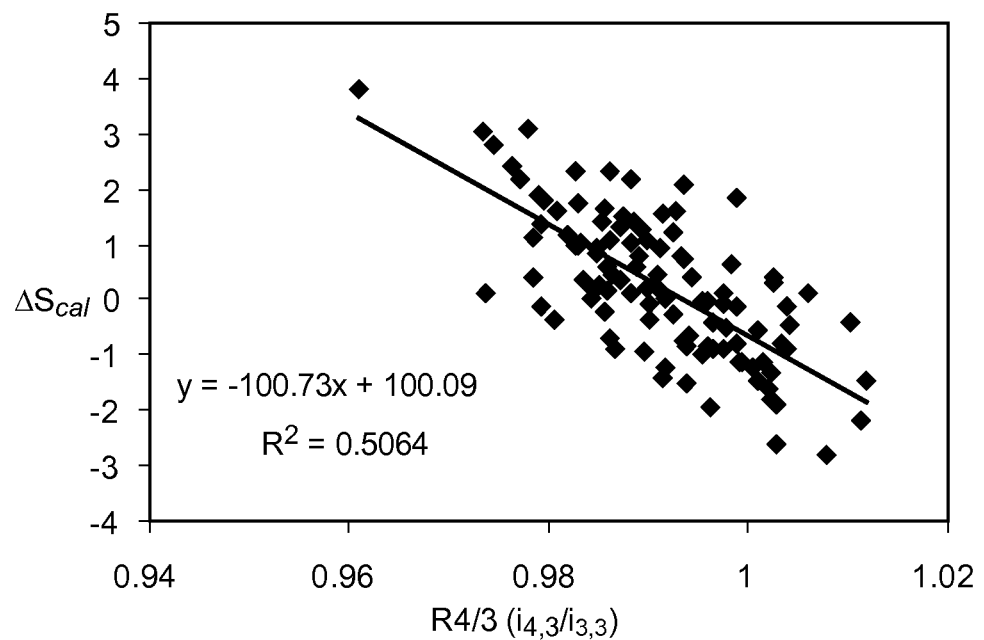
FIG. 11A depicts the correlation between $ΔS_{cal}$ and the error parameter R4/3.
Figure 11B:
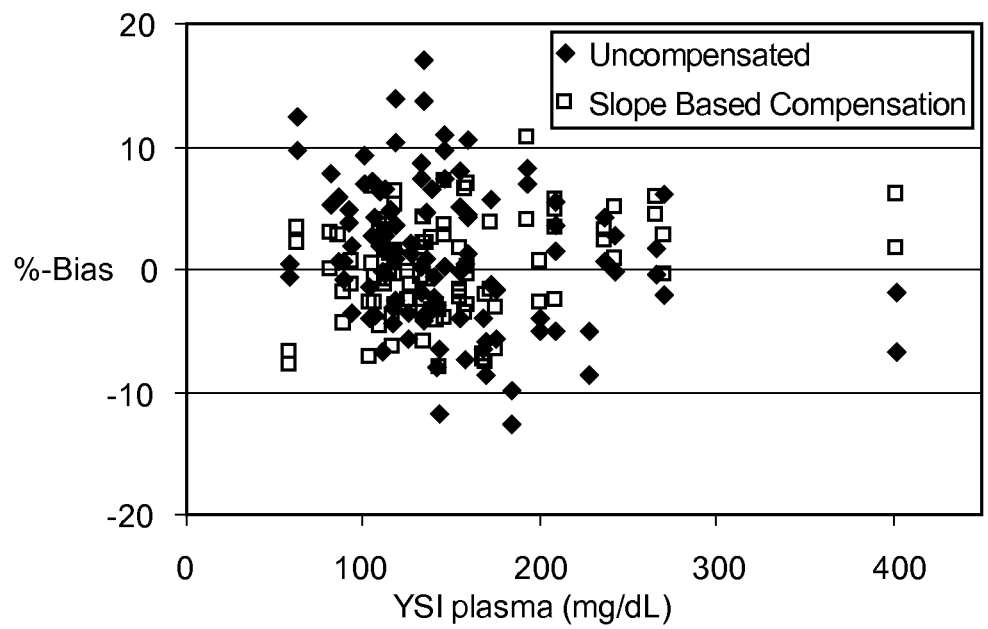
FIG. 11B depicts the distribution spread and percent of compensated and uncompensated concentration values falling within a ±10% bias limit.
Figure 11C:
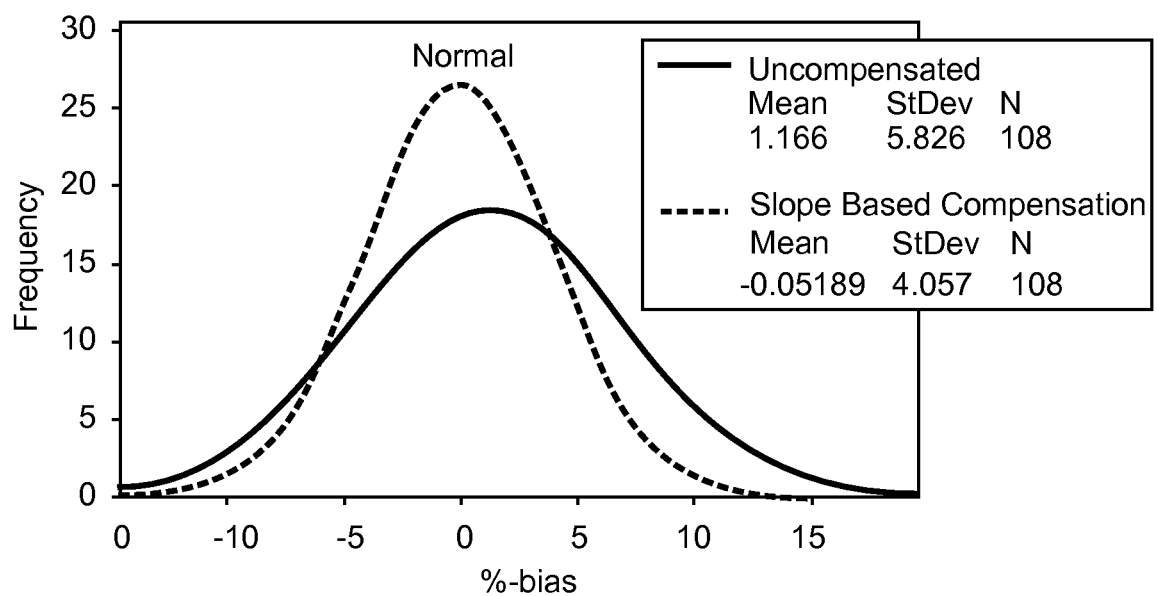
FIG. 11C depicts the improvement in the mean and standard deviation values for uncompensated and R4/3 error parameter compensated glucose concentration values.

FIG. 11A shows the correlation between $\Delta S_{cal}$ and the error parameter R4/3 for a biosensor system using reagents different that those seen in FIG. 9 or 10. Unlike for the FIG. 9 or 10 biosensor systems, for the FIG. 11A system, R4/3 provided a $R^2$ value of 0.5064. Thus, the bias associated with different biosensor system variables, such as a reagent composition, electrode structure, sensor strip construction, light-identifiable species, optical detection method, and the like, may be described by different error parameters. As shown in FIG. 11B, of the analyte concentrations determined with this system, 91.7% fell within the ±10% bias limit before compensation, while 99.1% of the analyte concentrations fell within the ±10% bias limit after compensation with the R4/3 error parameter. FIG. 11C shows the improvement in the mean and standard deviation values for uncompensated and R4/3 error parameter compensated glucose concentration values. As shown in the histogram, the standard deviation fell from 5.826 to 4.057 for the compensated concentration values, an improvement of about 30%.

Figure 12A:
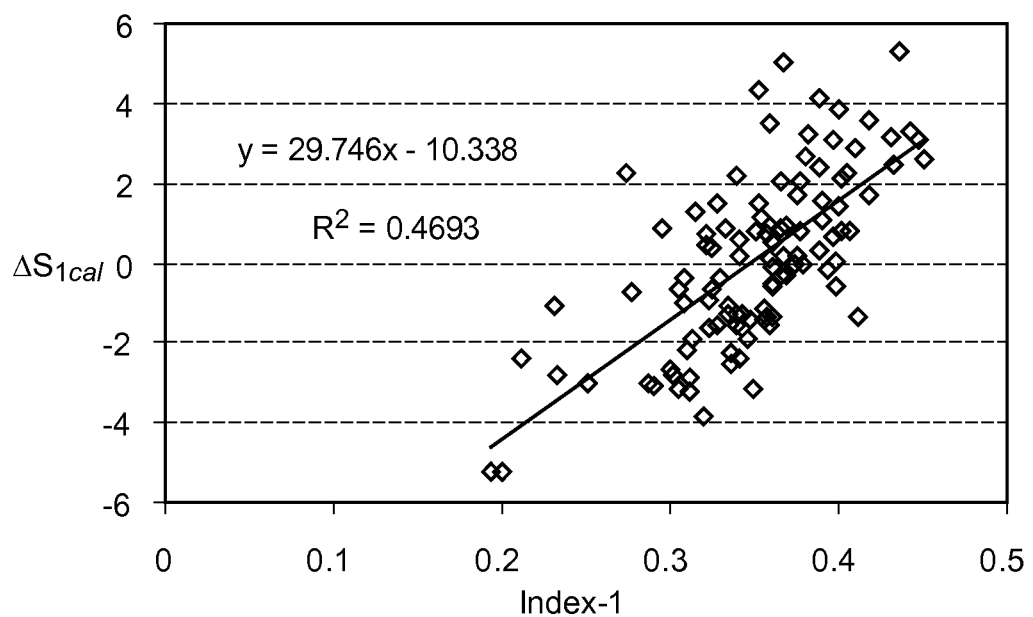
FIG. 12A depicts the correlation between $S_{1cal}$ and the error parameter Index-I.
Figure 12B:
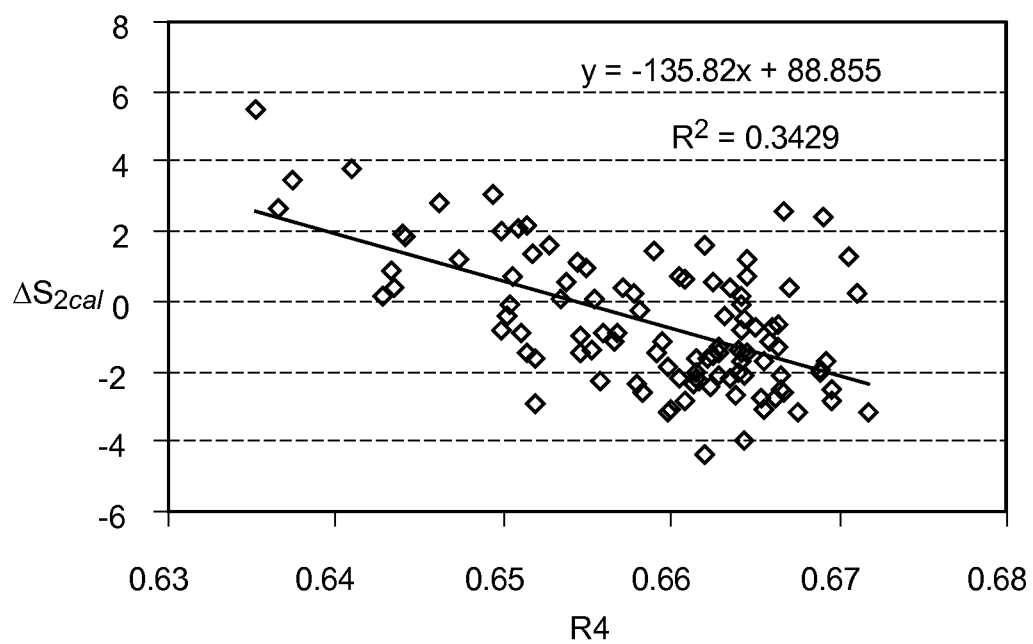
FIG. 12B depicts the correlation between $ΔS_{2cal}$ and the error parameter R4.

FIGS. 9, 10, and 11 used a single error parameter to determine a single $\Delta S$ value for compensation. FIG. 12A shows the correlation between $\Delta S_{1cal}$ and the error parameter Index-I ($R^2$=0.4693), while FIG. 12B shows the correlation between $\Delta S_{2cal}$ and the error parameter R4 ($R^2$=0.3429). $\Delta S_{1cal}$ was determined with Equation 9, while $\Delta S_{2cal}$ was determined with Equation 4. Of these two index functions, $\Delta S_1$ may be related to hematocrit, while $\Delta S_2$ may be related to other error contributors. When used in combination through Equation 5, the standard deviation of the percent bias decreased from 5.45 to 4.89 after compensation with the $\Delta S_1$ index function and to 3.99 after compensation with the $\Delta S_1$ and $\Delta S_2$ index functions. The $\Delta S_1$ index function provided an approximate 10% decrease in standard deviation, while the $\Delta S_1$ and $\Delta S_2$ index functions in combination provided an approximate 27% decrease. Thus, slope-based compensation increased the number of determined analyte concentrations falling within the ±10% bias limit to 99.1%, as shown in Table II, below.

TABLE II

| | Uncorrected | Corrected with $\Delta S_1$ | Corrected with $\Delta S_1$ and $\Delta S_2$ |
|---|---|---|---|
| % Bias Mean | 0.213 | −1.64 | −1.45 |
| Std. Dev. Of % Bias | 5.45 | 4.89 | 3.99 |

TABLE II-continued

| | Uncorrected | Corrected with $\Delta S_1$ | Corrected with $\Delta S_1$ and $\Delta S_2$ |
|---|---|---|---|
| % $A_{corr}$ within ±10% bias limit | 93.5 | 97.2 | 99.1 |

These results establish that an uncompensated analysis performed on multiple samples results in nearly 7% of the determined analyte concentration values falling outside of a ±10% bias limit, where after compensation less than 1% of the compensated values are outside of the limit. Using error parameters to determine $\Delta S$ values that are then used to compensate an analysis can provide increases in accuracy where at least 85% of the determined analyte concentration values preferably fall within a ±10% bias limit, and more preferably at least 90% of the determined analyte concentration values fall within a ±10% bias limit. At present, especially preferred slope-based bias correction methods can provide analyte concentration values where at least 95% or at least 97% of the determined analyte concentration values fall within a ±10% bias limit.

The slope deviation, $\Delta S$, and/or related index functions may be normalized to represent the %-bias in the correlation of analyte concentrations with output signals. In normalization, the slope deviation, index function, or other parameter is adjusted (multiplied, divided, or the like) by a variable to reduce the statistical effect of changes in the parameter, improve the differentiation in variations of the parameter, standardize measurements of the parameter, a combination thereof, or the like.

The slope deviation, $\Delta S$, in Equation 7 may be normalized by the slope of the reference correlation equation, $S_{cal}$, resulting in a compensation correlation between $\Delta S/S_{cal}$ and the index function.

In Equation 7, $\Delta S$ is divided by $S_{cal}$ as follows:

$$A_{corr} = \frac{i - Int}{S_{cal} + \Delta S} = \frac{i - Int}{S_{cal}(1 + \Delta S/S_{cal})}. \qquad \text{(Equation 14)}$$

$\Delta S/S_{cal}$ is an index function, f(index), which may be represented as follows:

$$\Delta S/S_{cal} = f(\text{Index}) = c_1 * \text{Index} + c_0 \qquad \text{(Equation 15)}.$$

The index function, f(index), of Equation 15 may be substituted into Equation 14 as follows:

$$A_{corr} = \frac{i - Int}{S_{cal} + (1 + f(\text{Index}))} \qquad \text{(Equation 16)}$$
$$= \frac{i - Int}{S_{cal}(1 + (c_1 * \text{Index} + c_0))}.$$

Solving for the slope deviation, $\Delta S$, provides the following relationship:

$$\Delta S = S_{cal} * f(\text{Index}) = S_{cal} * (c_1 * \text{Index} + c_0) \qquad \text{(Equation 17)}.$$

Figure 13A:
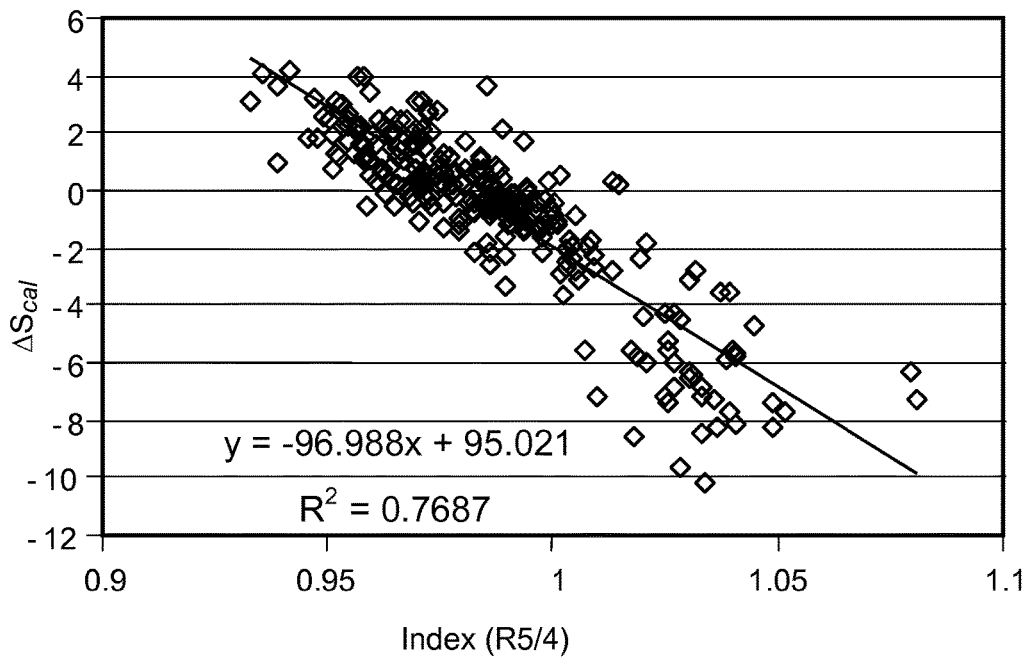
FIG. 13A depicts the correlation of $ΔS_{cal}$ with an index function responsive to the Ratio 5/4.
Figure 13B:
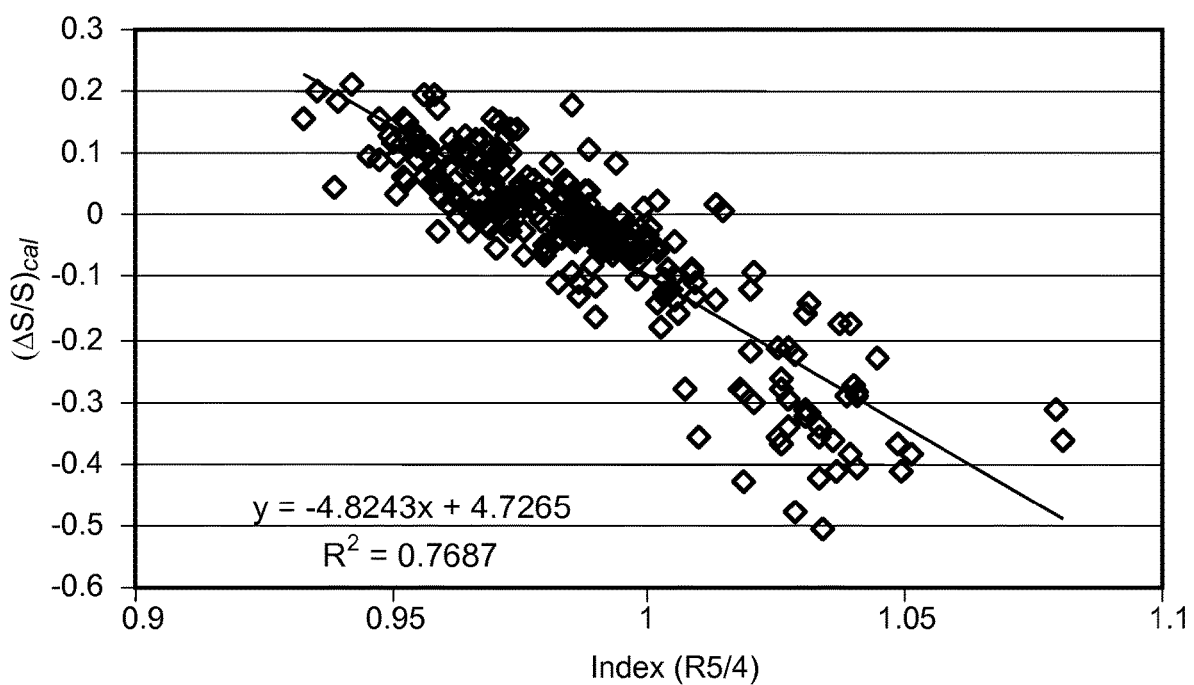
FIG. 13B depicts the correlation of $(ΔS'S)_{cal}$ with an index function responsive to the ratio R5/4.

The normalization of the slope deviation, $\Delta S$, by $S_{cal}$ essentially eliminates the potential effect from different calibrations of $S_{cal}$. FIG. 13A depicts the correlation of $\Delta S$ with an index function responsive to the ratio R5/4. FIG. 13B depicts the correlation of $\Delta S/S_{cal}$ with an index function responsive to the ratio R5/4.

The slope deviation, $\Delta S$, in Equation 7 also may be normalized by multiplication with a normalized slope function, $S_{NML}$, resulting in a compensation correlation between $S_{NML}$ and the index function.

The normalized slope function $S_{NML}$ may be represented as follows:

$$S_{NML} = S/S_{cal} \quad \text{(Equation 18)}$$
$$= \frac{i - Int}{A_{ref}} * \frac{1}{S_{cal}}$$
$$= f(\text{Index})$$
$$= d_1 * \text{Index} + d_0.$$

Substituting Equation 18 into Equation 7 and replacing $S_{NML}$ with an index function, f(index), results in the following relationship:

$$A_{corr} = \frac{i - Int}{S_{cal} * S_{NML}} \quad \text{(Equation 19)}$$
$$= \frac{i - Int}{S_{cal} * f(\text{Index})}$$
$$= \frac{i - Int}{S_{cal} * (d_1 * \text{Index} + d_0)}.$$

Figure 14:
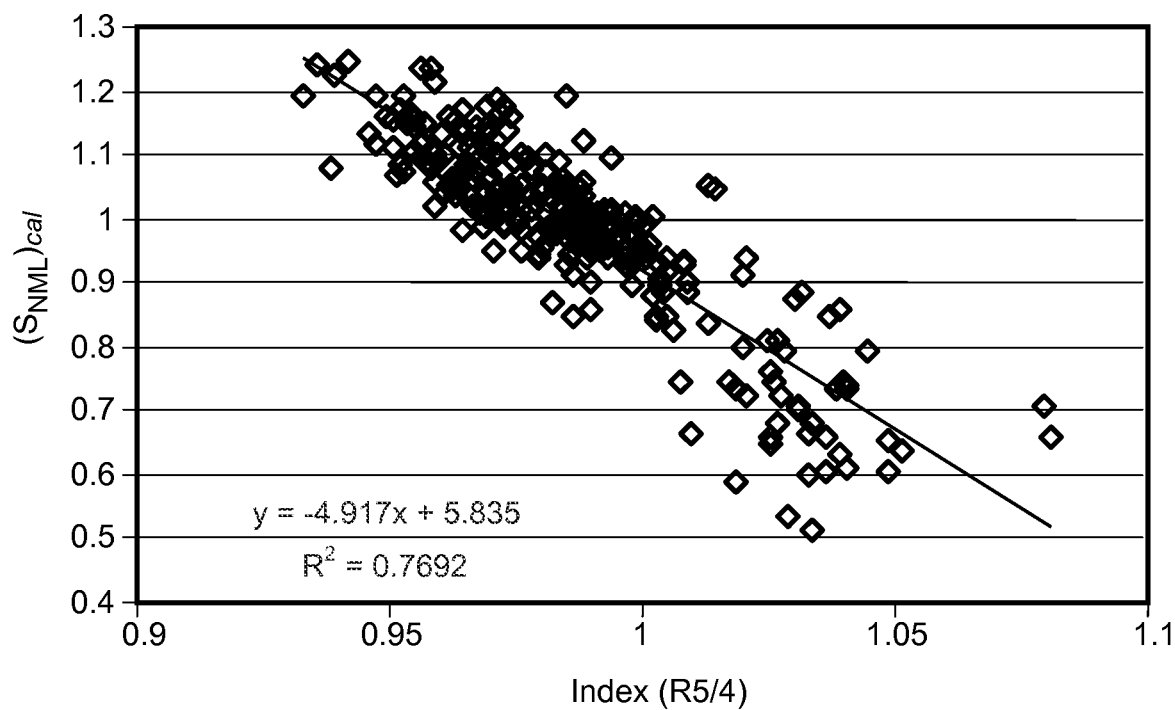
FIG. 14 depicts the correlation of $(ΔS/S)_{cal}$ with an index function responsive to the ratio R5/4.

FIG. 14 depicts the correlation of $S_{NML}$ with an index function responsive to the ratio R5/4. The correlations with the index functions in FIGS. 13A, 13B, and 14 are similar since all three index functions are mathematically related.

Similar to previous results, the normalized slope-based compensation increased the number of determined analyte concentrations falling within the ±10% bias limit to 99.1%, as shown in Table III, below.

TABLE III

|  | Uncorrected | Corrected with $\Delta S/S_{cal}$ | Corrected with $S_{NML}$ |
|---|---|---|---|
| % Bias Mean | 0.213 | −1.64 | −1.64 |
| Std. Dev. Of % Bias | 5.45 | 4.89 | 4.89 |
| % $A_{corr}$ within ±10% bias limit | 93.5 | 97.2 | 97.2 |

Figure 15:
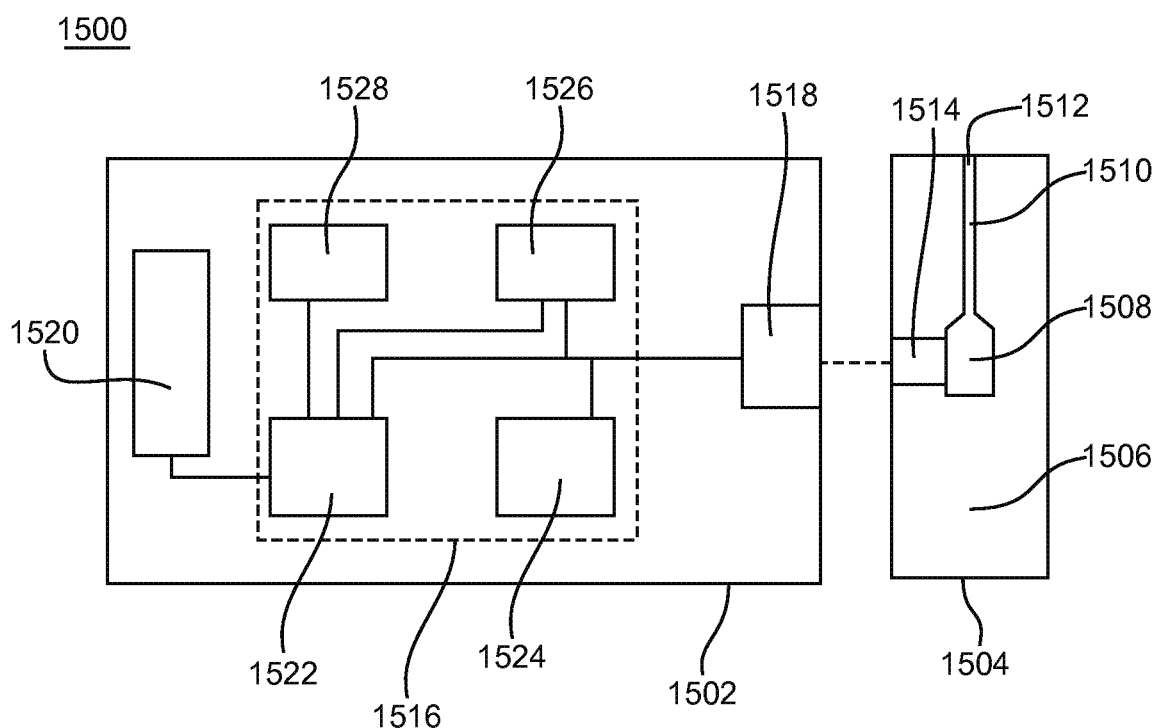
FIG. 15 depicts a schematic representation of a biosensor system that determines an analyte concentration in a sample of a biological fluid.

FIG. 15 depicts a schematic representation of a biosensor system 1500 that determines an analyte concentration in a sample of a biological fluid. Biosensor system 1500 includes a measurement device 1502 and a sensor strip 1504, which may be implemented in any analytical instrument, including a bench-top device, a portable or hand-held device, or the like. The measurement device 1502 and the sensor strip 1504 may be adapted to implement an electrochemical sensor system, an optical sensor system, a combination thereof, or the like. The biosensor system 1500 adjusts a correlation for determining analyte concentrations from output signals with at least one $\Delta S$ value. The $\Delta S$ adjusted correlations may improve the accuracy and precision of the biosensor system 1500 in determining the analyte concentration of the sample. The biosensor system 1500 may be utilized to determine analyte concentrations, including those of glucose, uric acid, lactate, cholesterol, bilirubin, and the like. While a particular configuration is shown, the biosensor system 1500 may have other configurations, including those with additional components.

The sensor strip 1504 has a base 1506 that forms a reservoir 1508 and a channel 1510 with an opening 1512. The reservoir 1508 and the channel 1510 may be covered by a lid with a vent. The reservoir 1508 defines a partially-enclosed volume. The reservoir 1508 may contain a composition that assists in retaining a liquid sample such as water-swellable polymers or porous polymer matrices. Reagents may be deposited in the reservoir 1508 and/or channel 1510. The reagents may include one or more enzymes, binders, mediators, and like species. The reagents may include a chemical indicator for an optical system. The sensor strip 1504 also may have a sample interface 1514 disposed adjacent to the reservoir 1508. The sample interface 1514 may partially or completely surround the reservoir 1508. The sensor strip 1504 may have other configurations.

In an optical sensor system, the sample interface 1514 has an optical portal or aperture for viewing the sample. The optical portal may be covered by an essentially transparent material. The sample interface may have optical portals on opposite sides of the reservoir 1508.

In an electrochemical system, the sample interface 1514 has conductors connected to a working electrode and a counter electrode. The electrodes may be substantially in the same plane or in more than one plane. Other separation distances between the electrodes and the lid may be used. The electrodes may be disposed on a surface of the base 1506 that forms the reservoir 1508. The electrodes may extend or project into the reservoir 1508. A dielectric layer may partially cover the conductors and/or the electrodes. The sample interface 1514 may have other electrodes and conductors.

The measurement device 1502 includes electrical circuitry 1516 connected to a sensor interface 1518 and a display 1520. The electrical circuitry 1516 includes a processor 1522 connected to a signal generator 1524, an optional temperature sensor 1526, and a storage medium 1528.

The signal generator 1524 provides an electrical input signal to the sensor interface 1518 in response to the processor 1522. In optical systems, the electrical input signal may be used to operate or control the detector and light source in the sensor interface 1518. In electrochemical systems, the electrical input signal may be transmitted by the sensor interface 1518 to the sample interface 1514 to apply the electrical input signal to the sample of the biological fluid. The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 1524 also may record an output signal from the sensor interface as a generator-recorder.

The optional temperature sensor 1526 determines the temperature of the sample in the reservoir of the sensor strip 1504. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 1528 may be a magnetic, optical, or semiconductor memory, another storage device, or the like. The storage medium 1528 may be a fixed memory device, a removable memory device, such as a memory card, remotely accessed, or the like.

The processor 1522 implements the analyte analysis and data treatment using computer readable software code and data stored in the storage medium 1528. The processor 1522 may start the analyte analysis in response to the presence of the sensor strip 1504 at the sensor interface 1518, the application of a sample to the sensor strip 1504, in response to user input, or the like. The processor 1522 directs the signal generator 1524 to provide the electrical input signal to the sensor interface 1518. The processor 1522 receives the sample temperature from the temperature sensor 1526. The processor 1522 receives the output signal from the sensor interface 1518. The output signal is generated in response to the reaction of the analyte in the sample. The output signal may be generated using an optical system, an electrochemical system, or the like. The processor 1522 determines $\Delta S$ compensated analyte concentrations from output signals using a slope-adjusted correlation equation as previously discussed. The results of the analyte analysis may be output to the display 1520 and may be stored in the storage medium 1528.

The correlation equations between analyte concentrations and output signals may be represented graphically, mathematically, a combination thereof, or the like. The correlation equations may be represented by a program number (PNA) table, another look-up table, or the like that is stored in the storage medium 1528. Instructions regarding implementation of the analyte analysis may be provided by the computer readable software code stored in the storage medium 1528. The code may be object code or any other code describing or controlling the functionality described herein. The data from the analyte analysis may be subjected to one or more data treatments, including the determination of decay rates, K constants, ratios, and the like in the processor 1522.

In electrochemical systems, the sensor interface 1518 has contacts that connect or electrically communicate with the conductors in the sample interface 1514 of the sensor strip 1504. The sensor interface 1518 transmits the electrical input signal from the signal generator 1524 through the contacts to the connectors in the sample interface 1514. The sensor interface 1518 also transmits the output signal from the sample through the contacts to the processor 1522 and/or signal generator 1524.

In light-absorption and light-generated optical systems, the sensor interface 1518 includes a detector that collects and measures light. The detector receives light from the liquid sensor through the optical portal in the sample interface 1514. In a light-absorption optical system, the sensor interface 1518 also includes a light source such as a laser, a light emitting diode, or the like. The incident beam may have a wavelength selected for absorption by the reaction product. The sensor interface 1518 directs an incident beam from the light source through the optical portal in the sample interface 1514. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The display 1520 may be analog or digital. The display may be an LCD display adapted to displaying a numerical reading.

In use, a liquid sample for analysis is transferred into the reservoir 1508 by introducing the liquid to the opening 1512. The liquid sample flows through the channel 1510, filling the reservoir 1508 while expelling the previously contained air. The liquid sample chemically reacts with the reagents deposited in the channel 1510 and/or reservoir 1508.

The sensor strip 1504 is disposed adjacent to the measurement device 1502. Adjacent includes positions where the sample interface 1514 is in electrical and/or optical communication with the sensor interface 1518. Electrical communication includes the transfer of input and/or output signals between contacts in the sensor interface 1518 and conductors in the sample interface 1514. Optical communication includes the transfer of light between an optical portal in the sample interface 1514 and a detector in the sensor interface 1518. Optical communication also includes the transfer of light between an optical portal in the sample interface 1514 and a light source in the sensor interface 1518.

The processor 1522 receives the sample temperature from the temperature sensor 1526. The processor 1522 directs the signal generator 1524 to provide an input signal to the sensor interface 1518. In an optical system, the sensor interface 1518 operates the detector and light source in response to the input signal. In an electrochemical system, the sensor interface 1518 provides the input signal to the sample through the sample interface 1514. The processor 1522 receives the output signal generated in response to the redox reaction of the analyte in the sample as previously discussed.

The processor 1522 determines the analyte concentration of the sample. The measurement device adjusts the correlation between analyte concentrations and output signals with at least one $\Delta S$ value. The analyte concentration is determined from the slope-adjusted correlation and the output signal.

Figure 16:
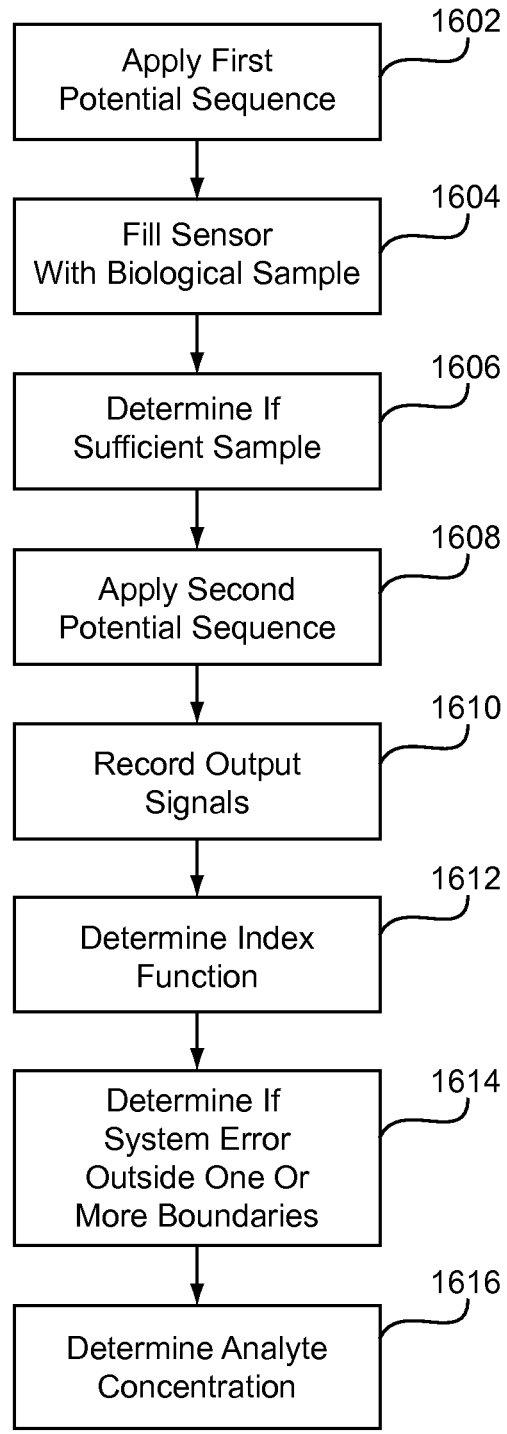
FIG. 16 represents another method for determining an analyte concentration in a sample of a biological fluid.

FIG. 16 represents another method for determining an analyte concentration in a sample of a biological fluid. In 1602, a biosensor system applies a first potential sequence across working and counter electrodes. The first potential sequence may be a polling potential or like sequence. The polling potential sequence may have an extended polling feature. In 1604, the biosensor is filled with a biological sample such as whole blood or the like as previously discussed. In 1606, the biosensor determines whether there is sufficient volume of the biological sample present in the sensor cell for analysis. The biosensor may determine whether currents or other output signals generated by the biological sample in response to the first potential sequence meet one or more thresholds at one or more polling potentials. In 1608, the biosensor system applies a second potential sequence. The biosensor system may apply the second potential sequence once the sensor cell is full. The second potential sequence may be responsive to gated amperometry or another electrochemical process. In 1610, the biosensor system records the output signals from the electrodes. In 1612, the biosensor system determines an index function in response to the output signals. The index function may include one or more indicator index values. The index function may be responsive a correlation based on %-bias, slope deviation, slope normalization, a combination thereof, or the like as previously discussed. The index function may represent a correlation between %-bias and a ratio of the output signals such as R5/4. In 1614, the biosensor system determines whether the system error is outside one or more error boundaries in response to the index function. In 1616, the biosensor system determines the analyte concentration in response to the output signals and the index function. The biosensor system adjusts the analyte correlation equation between the output signals and the analyte concentration in response to the index function, and then determines the analyte concentration using the adjusted or compensated analyte correlation equation. The biosensor system may adjust the analyte correlation equation when the index function indicates the system error is outside one or more error boundaries. The analyte correlation equation may be the slope of the correlation between the output signals and a reference analyte concentration.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method for determining an analyte concentration in a fluid sample via a biosensor system, comprising:
    providing an analyte measurement device and a sensor strip, the analyte measurement device including a storage device, a sensor interface, and a processor, the processor coupled to storage device and the sensor interface, the sensor interface for receiving the sensor strip, the sensor strip including an electrode that contacts the sensor interface of the measurement device when the sensor strip is placed in the sensor interface;
    applying an electrical input signal to the sample via the electrode of the sensor strip when the sensor strip is placed in the sensor interface of the analyte measurement device and a fluid sample is applied to the sensor strip;
    generating at least one output signal value from an analysis of the fluid sample via the sensor interface of the analyte measurement device, the at least one output signal value responsive to the analyte concentration in the sample;
    determining at least one $\Delta S$ value from at least one error parameter via the processor of the analyte measurement device, where the at least one $\Delta S$ value is a value of slope deviation or a value of normalized slope deviation in relation to at least one previously determined reference correlation relating previously determined reference output signal values to reference sample analyte concentration values, the previously determined reference sample analyte concentration values obtained from a reference instrument, the previously determined reference correlation stored in the storage device of the analyte measurement device, and where the at least one error parameter causes one or more errors in the at least one output signal value; and
    determining the analyte concentration in the sample from the at least one output signal value, the at least one $\Delta S$ value, and the at least one previously determined reference correlation relating the at least one output signal value to one of the reference sample analyte concentration values via the processor of the analyte measurement device,
        where the determining the analyte concentration in the sample comprises adjusting the at least one previously determined reference correlation with the at least one $\Delta S$ value, and
        where the determining the at least one $\Delta S$ value from at least one error parameter and the determining the analyte concentration in the sample from the at least one output signal value are performed by the processor of the analyte measurement device using computer readable software code.

2. The method of claim 1, where the fluid sample is a biological fluid.

3. The method of claim 1, where the analyte comprises glucose and the sample comprises whole blood.

4. The method of claim 1, where a percent bias of an absolute bias value over the reference value in the determined analyte concentration is at most ±10%.

5. The method of claim 1, where over 95% of the analyte concentrations determined from the method fall within a ±20% bias limit.

6. The method of claim 1, where the determining of the at least one $\Delta S$ value from the at least one error parameter includes determining the at least one $\Delta S$ value from at least one predetermined index function, the predetermined index function being determined by a regression equation of a plot between the deviation in a slope of the reference correlation in response to the at least one error parameter and, where the at least one predetermined index function is responsive to the at least one error parameter and provides the at least one $\Delta S$ value as a value of slope deviation or a value of normalized slope deviation in relation to the at least one previously determined reference correlation.

7. The method of claim 6, where the at least one error parameter is responsive to error contributors causing an alteration of the at least one output signal value.

8. The method of claim 6, where the at least one error parameter is selected from the group consisting of temperature and hematocrit level.

9. The method of claim 6, where when the at least one error parameter includes multiple error parameters, the multiple error parameters are independently responsive to different error contributors.

10. The method of claim 6, where the at least one error parameter has a correlation with a $\Delta S_{cal}$ value, the $\Delta S_{cal}$ value representing the difference between the reference correlation and a hypothetical perfect correlation having an $R^2$ value of at least 0.3.

11. The method of claim 6, where the at least one index function transforms the at least one error parameter into the at least one $\Delta S$ value.

12. The method of claim 1, where the input signal comprises pulsed electrical excitations.

13. The method of claim 1, where the output signal value is generated from light.

14. The method of claim 1, where the determining is represented as follows:

$$A_{corr} = \frac{i - Int}{S_{cal} + \Delta S}$$

where $A_{corr}$ is the determined analyte concentration, i is the at least one output signal value responsive to the analyte concentration in the sample, Int is an intercept from the at least one previously determined reference correlation, $S_{cal}$ is a slope from the at least one previously determined reference correlation, and $\Delta S$ is the at least one $\Delta S$ value.

15. The method of claim 1, where the at least one previously determined reference correlation and the at least one output signal value are modified with a second $\Delta S$ value, each $\Delta S$ value determined from a different predetermined index function, where the at least one index function is responsive to the at least one error parameter and provides a value of slope deviation or a value of normalized slope deviation in relation to the at least one previously determined reference correlation.

16. The method of claim 15, where different error parameters are transformed by the different index functions to provide the at least two ΔS values.

17. The method of claim 16, where a correlation between analyte concentration and the different error parameters is represented as follows:

$$A_{corr(2)} = \frac{i - Int}{S_{cal} + \Delta S_1 + \Delta S_2}$$

where $A_{corr(2)}$ is the analyte concentration corrected with two ΔS values and $\Delta S_1$ and $\Delta S_2$ are the at least two ΔS values.

18. The method of claim 17, where $\Delta S_1$ represents the error parameter responsive to an error contributor providing the largest bias in the determined analyte concentration.

19. The method of claim 14, further comprising determining the remaining system error values, $\Delta S_{2cal}$ is represented as follows:

$$\Delta S_{2cal} = S_{cal} * \left( \frac{A_{corr(1)}}{A_{ref}} - 1 \right),$$

where $\Delta S_{2cal}$ approximates the difference in slope between $S_{cal}$ and $S_{hyp}$ for a second error parameter after the first compensation, $S_{cal}$ is the slope from the at least one previously determined reference correlation, $S_{hyp}$ is a hypothetical slope of a line for the output signal value that provides an analyte concentration of the sample without error, $A_{corr(1)}$ is the analyte concentration represented by $A_{corr}$, and $A_{ref}$ is the reference sample analyte concentration value.

20. The method of claim 1, where the determining is with an equation relating percent bias to current.

21. The method of claim 1, where the sample is selected from the group consisting of a biological fluid, a derivative of a biological fluid, and combinations thereof.

22. The method of claim 1, where the measurement device is a portable measurement device.

23. The method of claim 1, further comprising normalizing the at least one ΔS value.

24. The method of claim 23, further comprising normalizing the at least one ΔS value in response to a slope of the at least one previously determined reference correlation.

25. The method of claim 23, further comprising normalizing the at least one ΔS value in response to a normalized slope function.

26. The method of claim 6, where the at least one predetermined index function is predetermined from normalized slope deviations with a calibration slope of the at least one previously determined reference correlation.

27. The method of claim 6, further comprising generating at least two output signal values from the sample,
where the at least two output signal values are responsive to the analyte concentration of the sample,
where the at least one predetermined index function represents a correlation between %-bias of the analyte concentration of the sample and a ratio of the at least two output signal values.

* * * * *